United States Patent

Bhandari et al.

[11] Patent Number: 6,006,582
[45] Date of Patent: Dec. 28, 1999

[54] HYDROGEN SENSOR UTILIZING RARE EARTH METAL THIN FILM DETECTION ELEMENT

[75] Inventors: Gautam Bhandari, Danbury; Thomas H. Baum, New Fairfield, both of Conn.

[73] Assignee: Advanced Technology Materials, Inc., Danbury, Conn.

[21] Appl. No.: 09/042,698

[22] Filed: Mar. 17, 1998

[51] Int. Cl.$^6$ .............. G01N 7/00; G01N 21/00; G01N 30/96; H01L 47/00
[52] U.S. Cl. .............. 73/23.2; 73/31.06; 422/57; 422/88; 257/2
[58] Field of Search .............. 73/23.2, 31.06, 73/31.05; 422/57, 86, 88; 257/2, 4, 107, 108; 338/34

[56] References Cited

U.S. PATENT DOCUMENTS

| | | | |
|---|---|---|---|
| 3,768,975 | 10/1973 | Toy | 422/57 |
| 3,951,603 | 4/1976 | Obayashi et al. | 23/232 E |
| 3,953,173 | 4/1976 | Obayashi et al. | 23/232 E |
| 4,574,095 | 3/1986 | Baum et al. | |
| 4,661,320 | 4/1987 | Ito et al. | 422/86 |
| 4,836,012 | 6/1989 | Doty et al. | 73/31.06 |
| 4,892,834 | 1/1990 | Rauh | 436/149 |
| 5,134,248 | 7/1992 | Kiec et al. | 174/84 R |
| 5,520,753 | 5/1996 | Hunter | 148/430 |
| 5,635,729 | 6/1997 | Griessen et al. | 257/2 |
| 5,668,301 | 9/1997 | Hunter | 73/23.2 |
| 5,670,115 | 9/1997 | Cheng et al. | 422/90 |
| 5,733,506 | 3/1998 | Silver et al. | 422/90 |

FOREIGN PATENT DOCUMENTS

WO 96/38758  12/1996  WIPO .............. G02F 3/02

OTHER PUBLICATIONS

Huiberts, J.N.,; Griessen, R.; Rector, J.R.; Wijngaarden, R.J.; Dekker, J.P.; deGroot, D.G.; Koeman, N.J. "Yttrium and Lanthanum Hydride Films with Switchable Optical Properties", *Nature*, 1996, vol. 380, pp. 231–234.

Yannopoulos, L.N.; Edwards, R.K.; Wahlbeck, P.G., "The Thermodynamics of the Yttrium–Hydrogen System", *J. Phys. Chem.* 1965, vol. 69, pp. 2510–2515.

Flotow,H.E.; Osborne, D.W.; Otto, K.; Abraham, B.M., "$YH_3$ and $YD_3$: Heat Capacities and Thermodynamic Functions from 15° to 350° K and Infrared Absorption Spectra", *J Chem. Phys.* 1963, vol. 38, pp. 2620–2626.

Vajda, P. in Handbook on the Physics and Chemistry of Rare Earths, vol. 20 (eds Gschneidner, K.A.; Eyring, L.) Amsterdam, Elsevier, 1995, pp. 207–291.

(List continued on next page.)

*Primary Examiner*—Hezron Williams
*Assistant Examiner*—Jay L. Politzer
*Attorney, Agent, or Firm*—Steven J. Hultquist; Oliver A.M. Zitzmann

[57] ABSTRACT

A hydrogen sensor for the detection of hydrogen, e.g., in an environment susceptible to the incursion or generation of hydrogen. The sensor includes a rare earth metal thin film arranged for exposure to the environment and exhibiting a detectable change of physical property, e.g., optical transmissivity, electrical resistivity, magneto-resistance, and/or photoconductivity, when the rare earth metal thin film is contacted with hydrogen gas. The sensor may include an output assembly for converting the physical property change to a perceivable output. The rare earth metal thin film may correspondingly be used for signal processing applications, in which the rare earth metal thin film is contacted with hydrogen gas, and a predetermined voltage signal is selectively imposed across the rare earth metal thin film, to selectively electrically switch the film between mirror and window states, with a response being generated according to which of the mirror and window states is present.

49 Claims, 7 Drawing Sheets

OTHER PUBLICATIONS

Mueller, W.M.;Blackledge, J.P.; Libowitz, G.G. in Metal Hydrides (eds Mueller, W.M.;Blackledge, J.P.; Libowitz, G.G.) New York, Academic, 1968, Ch. 9 & 10.

Encyclopedia of Inorganic Chemistry, ed. R.Bruce King, John Wiley & Sons, NY, vol. 6, pp. 3010–3011.

e–mail forwarded to Greg Hall (NASA Technical Monitor) on May 29, 1997.

Chenier, J.P. in Survey of Industrial Chemistry, New York, VCH, 1992, p. 60.

Ahuja, R.; Johansson, B.; Wills, J.M.; Eriksson, O. "On the Semiconducting State and Structural Properties of $YH_3$ from First Principles Theory"" *Appl. Phys. Lett.*, 1997, vol. 71, No. 24, pp. 3498–3500.

Van der Sluis, P.; Ouwerkek, M.; Duine, P.A., "Optical Switches Based on Magnesium Lanthanide Alloy Hydrides", *Appl. Phys. Lett.* 1997, vol. 70, No. 25, pp. 3356–3358.

Notten, P.H.L.; Kremers, M.; Griessen, R., "Optical Switching of Y–Hydride Thin Film Electrodes", *J. Electrochem. Soc.* 1996, vol. 143, No. 10, pp. 3348–3353.

Vourvoulias, B.; Kwon, B., "Now You See it", *Newsweek*, 1998, Mar. 2, 1998, p. 13.

Freemantle, M., "Hydride Fims Display Mirror–Window Changes", *C&EN*, 1996, p. 9.

Evans, W.J. ; Drummond, D. K. ; Hanusa, T.P.; Doedens, R.J. Bis(1,3–dimethylcycloentadienyl)yttrium Complexes. Synthesis and X–ray Crystallographic Characterization of $[(1,3-Me_2C_5H_3)_2Y(\mu-Me)]_2$, $[(1,3-Me_2C_5H_3)_2Y(\mu-Me)]_3$, and $[(1,3-Me_2C_5H_3)_2(THF)Y(\mu-Me)]_2$, *Organmetallics* 1987, vol. 6, pp. 2279–2285.

Jeske, G.; Lauke, H.; Mauermann, H.; Swepston, P.N.; Schumann, H.; Marks, T.J., "Highly Reactive Organolanthanides. Systematic Routes to and Olefin Chemistry and Late Bis(pentamethylcyclopentadienyl) 4f Hydrocarbyl and Hydride Cmplexes", *J. Am. Chem. Soc.* 1985, vol. 107, pp. 8091–8103.

Wilkinson, G.; Birmingham, J.M., "Cycloppentadienyl Compounds of Sc, Y, La, Ce and Some Lanthanide Elements", *J. Am. Chem. Soc.* 1954 vol. 76, p. 6210.

Wayda, A.L., "Mono–, bis– and tris(t–butylcyclopentadienyl)lanthanoid Complexes", *J. Organomet. Chem.* 1989, vol. 361, p. 73.

Tsutsui, M.; Gysling, H.J., "A New Series of Organolanthanides: $Ln(indenyl)_3$", *J. Am. Chem. Soc.* 1969, vol. 91, pp. 3175–3178.

Schulz, D.L.; Hinds, B.J.; Neumayer, D.A.; Stern, C.L.; Marks, T.J.., "Barium β–Ketoiminate Complexes Containing Appended Ether Lariats. Synthesis, Characterization, and Implementation as Fluorine Free Barium MOCVD Precursors", *Chem. Mater.* 1993, vol. 5, pp. 1605–1617.

McGeachin, S.G., "Synthesis and Properties of Some B–Diketimines Derived From Acetylacetone, And Their Metal Complexes", *Can. J. Chem.* 1968, vol. 46, pp. 1903–1912.

Van Buskirk, P.C.;Kirlin, P.S.., "$BaTiO_3$—$SrTiO_3$ DRAM's Final Report", *Phase I Final Report,* Contract #DNA001–91–C–0078, Feb., 1991.

Zhang, J.; Gardiner, R.; Kirlin, P.S., Layered Superconductors: Fabrication, Properties and Applications, ed. D.T. Shaw and T.R. Schneider, MRS Proceedings, 1992, vol. 275, p. 419.

Bhandari, Gautam, P.I., "Lightweight and Inexpensive Hydrogen Selective Sensor", NASA SBIR Phase II, Sep. 16, 1997, Proposal No., 96–1–Phase II 16.12 1100, pp. 1–46.

Bhandari, Gautam, P.I., "Lightweight and Inexpensive Hydrogen Selective Sensor", NASA SBIR 96–1 Solicitation, Aug. 27, 1996, Proposal No., 96–1–16.12 1100, pp. 1–24.

"Phase Change Materials lead to Hydrogen Sensors" by Bhandari, Gautam, Sensor Technology, vol. 13, No. 8, pp. 1–2, (May, 1997).

HYDROGEN SENSOR UTILIZING RARE EARTH METAL THIN FILM DETECTION ELEMENT

BACKGROUND OF THE INVENTION

1. Field of the Invention

The present invention relates to a rare earth metal thin film sensor for detecting hydrogen, and to a differential sensing method for determining the presence of hydrogen in an environment potentially containing same.

2. Description of the Related Art

Hydrogen is a flammable and explosive gas with a wide variety of industrial and scientific uses. Illustrative industrial uses include the production of ammonia, ethanol, methanol, aniline and hydrogen chloride; hydroforming, hydrocracking and hydrorefining of petroleum; hydrogenation of vegetable oils; and reduction of metallic ores.

In space flight applications, $H_2/O_2$ mixtures are used in large quantities as propellants for vehicular propulsion systems.

Hydrogen is also used in a variety of metal forming and microelectronic processing steps that rely upon the use of hydrogen of hydrogen containing gases (i.e., forming gases). These processes are often critical in device fabrication and metal interconnect processing of multi-level devices.

In these and other applications, hydrogen sensors are employed to monitor the environment of the process system in which hydrogen is utilized, to safeguard the apparatus and associated operating personnel, as well as to ensure the efficiency and operational integrity of the system. For such purpose, a variety of hydrogen sensors and elaborate detection schemes have been employed and are in common use.

Most of the currently used hydrogen sensors employ sensing arrangements developed several decades ago. A variety of these commercially available hydrogen sensors are based on measuring an electrical characteristic (e.g., resistance) across a sensor element.

The most popular hydrogen sensor is the "catalytic combustible" or "hot wire" sensor (CC sensor).

The CC sensor consists of two beads of resistive elements (Pt/Ir wire) arranged in a Wheatstone bridge configuration and heated to 600–800° C. One bead is coated with a reactive catalyst, while the other is not. Gas is sampled over the beads either by diffusion or by a pump.

In the presence of a flammable gas, the heat of oxidation raises the temperature of the bead and the associated heater element and alters the electrical resistance characteristics of the Wheatstone bridge circuit. This resistance change is related to the concentration of all flammable gases (including $H_2$) in the vicinity of the sensor.

Unfortunately, in $O_2$ deficient environments or above the upper explosive limit, the oxidation process is quenched. This causes the heating element of the CC sensor to cool and the needle of the device to fluctuate downward (evidencing a zero or negative value).

Further, since the CC sensor is based upon oxidation, virtually any and all hydrocarbons have the same response.

A further difficulty is that the CC sensor element can be contaminated by halogenated hydrocarbons or poisoned by silicones, lead and phosphorous.

A second commonly used $H_2$ sensor is a metal oxide semiconductor (MOS) sensor, in which the sensor element consists of mixed Fe, Zn and Sn oxides and is heated to a temperature of 150–350° C. Oxygen atoms absorb on the MOS surface of the sensor element to create an equilibrium concentration of oxide ions in the surface layers.

The baseline resistance (or conductivity) of the MOS sensor in "clean air" is first established by calibration. When certain toxics (e.g., CO or $H_2S$) or hydrocarbons come in contact with the sensor, they absorb on the surface of the MOS element. This absorption shifts the oxygen equilibrium, causing a detectable decrease in resistance of the MOS material.

MOS hydrogen sensors have a number of operational deficiencies. They require frequent calibrations (e.g., approximately every 3 months for current commercially available models), exhibit unacceptable response times (3–5 minutes) for rapid detection, can be the source of ignition and fires/explosions, and are incompatible with halogenated vapors.

An important limitation of the above-described commercially available hydrogen sensors is that they are not $H_2$ specific. All volatile organic compounds (e.g., pentane, toluene, acetone, etc.) as well as gases containing hydrogen (e.g., $H_2S$ and ethylene) will react with the sensor materials in the sensing elements of these detectors, thereby providing false readings.

A further difficulty with currently available $H_2$ sensors is that they are often incapable of effectively monitoring process gas streams containing mixtures that include $H_2$. Such multicomponent gas streams are commonly analyzed by batch gas chromatography and mass spectrometry (GC/MS)—a comparatively expensive and time-consuming process.

These commercially available hydrogen sensors, in addition to being non-discriminating (non-selective) for hydrogen, and susceptible to being easily poisoned, are also bulky, consume a considerable amount of electric power and require frequent calibrations.

Against these many disadvantages and limitations of currently available hydrogen sensors, a major advance is needed in hydrogen sensor technology to overcome such limitations. Among the needed improvements in the field is the provision of $H_2$ sensors capable of detecting hydrogen in cold and oxygen deficient (helium rich) environments such as in outer space. An $H_2$ sensor is also needed that eliminates the risk of accidental explosions associated with the use of electric current in presently available sensors. Moreover, a low cost, lightweight, miniature, and hydrogen-specific sensor is highly desirable.

It therefore is an object of the present invention to provide an improved hydrogen sensor and hydrogen sensing methodology overcoming the aforementioned deficiencies of the prior art $H_2$ detectors.

Other objects and advantages of the present invention will be more fully apparent from the ensuing disclosure and appended claims.

SUMMARY OF THE INVENTION

In one aspect, the present invention relates to a hydrogen sensor for the detection of hydrogen, e.g., in an environment susceptible to the incursion or generation of hydrogen. The sensor comprises a rare earth metal thin film arranged for exposure to the environment and exhibiting a detectable change of physical property when the rare earth metal thin film is exposed to hydrogen.

Another aspect of the invention relates to a switching device including a rare earth metal thin film, a source of hydrogen in contact with the film, and an electrical driver arranged to selectively impose a predetermined voltage across the rare earth metal thin film, to selectively electrically switch the film between window and non-window states.

The invention in a further aspect relates to a hydrogen detection system for monitoring an extended or remote area region for the incursion or generation of hydrogen therein, said hydrogen detection system comprising a multiplicity of rare earth metal thin film detector elements each of which (i) is arranged for exposure to a specific individual locus of the extended area region and (ii) exhibits a detectable change of physical property when the rare earth metal thin film of the detector element is contacted with hydrogen at said locus.

Yet another aspect of the invention relates to a method of fabricating a hydrogen sensor, comprising forming on a substrate a rare earth metal thin film which responds to contact with hydrogen by exhibiting a detectable change of at least one physical property, and coupling the thin film with means for outputting the detectable physical property change when the rare earth metal thin film is contacted with hydrogen.

In one method aspect, the invention relates to a method of detecting hydrogen in an environment, comprising:

providing a hydrogen sensor comprising a rare earth metal thin film arranged for exposure to the environment and exhibiting a detectable change of physical property when the rare earth metal thin film is exposed to hydrogen;

exposing the rare earth metal thin film to the environment; and monitoring said physical property to determine the presence of hydrogen in the environment.

A further aspect of the invention relates to a method of signal processing, comprising:

providing a rare earth metal thin film, exposing the rare earth metal thin film to hydrogen;

selectively imposing a predetermined voltage signal across the rare earth metal thin film, to selectively electrically switch the film between non-window and window states; and generating an output in response to which one of said non-window and window states is present.

The present invention additionally contemplates in another aspect a structural member selectively variable between window and non-window states, comprising:

a rare earth metal thin film, a source of hydrogen for contacting the rare earth metal thin film, and an electrical driver circuit which is selectively actuatable to selectively impose a predetermined voltage signal across the rare earth metal thin film, to responsively place the rare earth metal thin film in a selected one of the window and non-window states.

Other objects and advantages of the invention will be more fully apparent from the ensuing disclosure and claims.

DETAILED DESCRIPTION OF THE INVENTION, AND PREFERRED EMBODIMENTS THEREOF

Figure 1:
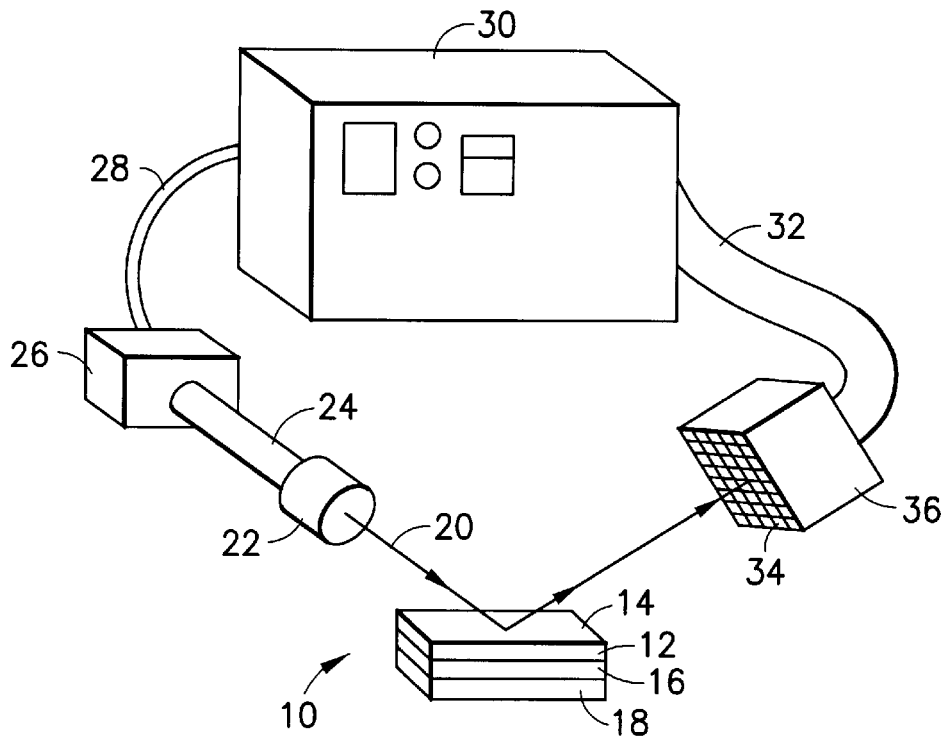
FIG. 1 is a schematic representation of a hydrogen sensor according to one embodiment of the invention, in a non-hydrogen environment.

The present invention makes use of the fact that upon exposure to hydrogen, rare earth thin films exhibit striking changes in physical properties, such as optical properties, changing from metallic (opaque) to semiconducting (transparent) phases. These optical changes are accompanied by changes in electrical resistivity, magneto-resistance and photoconductivity of the hydrogenated rare earth thin film.

The invention thus contemplates various sensor devices and apparatus, as well as methodology which utilize rare earth metal thin films with which hydrogen is interactive to produce both a physical and chemical change in the properties of the rare earth metal thin film.

In the preferred practice of the invention, as hereinafter more fully described, the rare earth metal thin film is overlaid by a protective overlayer which is hydrogen-permeable, but which is at least highly impermeable to reactive species that could otherwise deleteriously interact with the rare earth metal thin film and prevent it from producing the desired physical property change of the film upon exposure of hydrogen therewith.

As used herein, the term "rare earth metal" means a metal selected from scandium, yttrium, lanthanum, the lanthanides, and the actinides, as well as alloys and combinations of such metals, and alloys and combinations of such metals with Group II elements calcium, barium, strontium and magnesium. The lanthanides are the 14 elements following lanthanum in the Periodic Table, viz., cerium, praseodymium, neodymium, promethium, samarium, europium, gadolinium, terbium, dysprosium, holmium, erbium, thulium, ytterbium and lutetium. The actinides are the elements of the Periodic Table having the atomic numbers 89 through 103 inclusive, viz., actinium, thorium, protactinium, uranium, neptunium, plutonium, americium, curium, berkelium, californium, einsteinium, fermium, mendelevium, nobelium and lawrencium.

The physical property altered in response to the presence of hydrogen may be the optical transmissivity of the film to optical radiation incident on the sensor element, or electrical resisitivity as hereinafter more fully described. The change in physical property of the rare earth metal thin film is readily monitored, to provide an output indicative of the presence of hydrogen in the environment to which the rare earth metal thin film is exposed.

The aforementioned optical changes in rare earth thin films, incident to their exposure to hydrogen, result from a chemical equilibrium between the dihydride and trihydride forms.

The dihydride form of the rare earth thin film is opaque and reflecting, whereas the trihydride form of the film is transparent. When hydrogen is present, a dynamic equilibrium exists between the two forms and the physical and optical changes can be quite dramatic.

For example, in the presence of hydrogen, noble metal (e.g., Pd, Pt) overcoated Y reacts to form the dihydride ($YH_2$).

Further exposure to hydrogen results in the formation of the trihydride $YH_3$. This second step occurs at room-temperature and ambient pressure and is completely reversible.

The formation of $YH_2$, on the other hand, is essentially irreversible as a result of its relatively large heat of formation (−114 kJ/mol H) compared with the equilibrium step (−41.8 kJ/mol H or −44.9 kJ/mol H). This process is illustrated in the following formula:

The transition of the reflecting rare earth dihydride to the transparent rare earth trihydride is a chemical change with electronic origins. The dark blue reflecting phase of $YH_2$ is metallic, whereas the transparent phase ($YH_3$) is semiconducting with a direct band gap of 1.8 eV. This change of state—from metallic to semiconducting—can therefore be readily quantified by measuring the resistance of the film under hydrogen exposure conditions. Resistance measurements allow the correlation of the optical and electrical behavior of the films.

Unlike currently available sensors, the sensors of the present invention provide the capability of higher sensitivity at lower temperatures without the use of electrical circuitry that may provide a source for ignition. Qualitatively this is due to the fact that the rare earth dihydride to trihydride transition is an exothermic chemical reaction (negative ΔG: −41.8 kJ/mol H or −44.9 kJ/mol H). Thus, at lower temperatures the equilibrium favors the trihydride form. In addition, absorption of gases onto solids is favored at lower temperatures. Lower temperatures will therefore lead to a higher concentration of $H_2$ in the film resulting in a faster reaction with $YH_2$.

The dihydride to trihydride transition can also be induced by changing the voltage in an electrolytic cell. While we do not wish to be bound by any theory as regards the specific mode or mechanism of behavior of the rare earth thin film sensors in accordance with the present invention, it is believed that a metal-insulator transition rather than a structural phase change causes the observed optical transformation.

In accordance with the invention, this metal-insulator transition may be employed in solid state devices that electrically switch hydride films between mirror and window states, in which the rare earth thin film is arranged with an electrical driver to selectively alter the specific state of the film, for signal processing or display applications.

Such switching capability of rare earth thin films may therefore be employed for routing optical signals in high speed communication networks. Rare earth thin films switching assemblies may therefore be used in diverse applications such as optical communications, optoelectronics, display technologies, laser technology, architectural glass applications, flat panel displays, automotive applications and photography.

As another application in the broad practice of the invention, the rare earth thin films may be utilized for glass or window applications, such as architectural glass applications, automotive and other vehicular glass applications, goggles, visors, and other eyewear, etc.

In hydrogen sensing applications, one advantage of rare earth thin film $H_2$ sensors of the present invention is that their reliance on an optical transition allows quick and reliable $H_2$ detection without the complexity and hazards inherent in reactive hydrogen sensors which rely on an electrical charge. A further advantage of reliance on an optical transition is that the size, weight and design of the sensor can be greatly simplified and miniaturized. Rare earth thin films also enable the use of very simple sensors and analytical instrumentation.

The selectivity exhibited by rare earth thin films allows, for the first time, fabrication of inexpensive optical sensors that can be deployed in large numbers to remotely monitor hydrogen levels over large areas. Furthermore, as discussed in greater detail hereinafter, rare earth thin films can operate in an industrial or manufacturing environment containing trace organic vapors. We are not aware of any existing hydrogen sensing technologies providing all of these attributes.

Rare earth thin films can be coated with materials such as palladium or platinum to provide an effective barrier to oxidation, yet enable hydrogen to diffuse through to the rare earth thin film, thereby acting as a selective membrane for hydrogen in the sensor element.

The deposition of rare earth thin films on substrates may be readily carried out using organometallic precursors that thermally decompose to the metal hydride or elemental metal in a reducing environment of hydrogen. Under some conditions, the direct formation of rare earth metal hydride materials may be realized.

The invention enables the fabrication of switching devices including rare earth metal thin films, a source of hydrogen in contact with the film, and an electrical driver arranged to selectively impose a predetermined voltage across the rare earth metal thin film, to selectively electrically switch the film between mirror and window states. The source of hydrogen may be hydrogen gas supplied for contacting with the rare earth metal thin film, or alternatively the hydrogen may be present in the form of a hydride that supplies hydrogen to the rare earth thin film for such purpose.

The invention also enables a hydrogen detection system to be constructed for monitoring an extended or remote area region for the incursion or generation of hydrogen therein. The hydrogen detection system includes a multiplicity of rare earth metal thin film detector elements each of which (i) is arranged for exposure to a specific individual locus of the extended area region and (ii) exhibits a detectable change of physical property, e.g., optical transmissivity, electrical resistivity, magneto-resistance and/or photoconductivity, when the rare earth metal thin film of the detector element is contacted with hydrogen gas at such locus.

The hydrogen detection system described in the preceding paragraph may be constructed and arranged so that different physical properties are detected when multiple detector elements are contacted with hydrogen gas at different loci of the extended area region.

The hydrogen sensor of the invention is readily fabricated by forming on a substrate a rare earth metal thin film which is responsive to contact with hydrogen by exhibiting a detectable change of physical property, and coupling the thin film with means for exhibiting the detectable change of physical property when the rare earth metal thin film is exposed to hydrogen.

The means for exhibiting the detectable change of physical property when the rare earth metal thin film is contacted with hydrogen gas, may for example comprise a colored substrate, whereby the detectable change of physical property entails a change from opacity to transparency when the rare earth metal film is contacted with hydrogen gas or a change in color as determined by the colored layer in close proximity to the hydrogen sensitive layer (lanthanum hydride film) in its transmissive form. By such arrangement, the colored substrate is obscured in the absence of hydrogen, and rendered visible when hydrogen is present and converts the formerly opaque film to a transparent film.

The means for exhibiting the detectable change of physical property when the rare earth metal thin film is contacted with hydrogen gas, may include suitable circuit means for signal processing the change of physical property and generating an output indicative of the presence or absence of hydrogen gas.

In the sensor of the invention, the rare earth metal thin film may be formed on the substrate by a technique such as physical vapor deposition, chemical vapor deposition, sputtering, solution deposition, focused ion beam deposition, electrolytic plating, and electroless plating. Preferably, the rare earth metal thin film is formed on the substrate by physical vapor deposition, or alternatively by chemical vapor deposition, e.g., by liquid delivery chemical vapor deposition, using an organometallic precursor that thermally decomposes to the metal hydride or elemental metal in a reducing environment of hydrogen.

The rare earth metal thin film in the sensor may in one embodiment include a rare earth metal component such as a trivalent rare earth metal, e.g., yttrium or lanthanum, that is reactive with hydrogen to form both metal dihydride and metal trihydride reaction products, wherein the metal dihydride and metal trihydride reaction products have differing physical properties. The physical property change may for example include an optical transmissivity change, such as a change of optical opacity to optical transparency when the rare earth metal thin film is contacted with hydrogen gas. The physical property change may comprise a change from a metallic state to a semiconducting state, whereby the step of monitoring the physical property to determine the presence of hydrogen gas in the environment may be carried out by monitoring the electrical resistance of the rare earth metal thin film.

The rare earth metal thin film may be overlaid with a hydrogen-permeable material constituting a barrier to contact of the rare earth metal thin film with oxidizing species from the environment prior to the step of monitoring said physical property to determine the presence of hydrogen gas in the environment.

The rare earth metal thin film in the broad practice of the invention may suitably comprise at least one metal selected from the group consisting of:

(I) scandium, yttrium, lanthanum, cerium, praseodymium, neodymium, promethium, samarium, europium, gadolinium, terbium, dysprosium, holmium, erbium, thulium, ytterbium, lutetium, actinium, thorium, protactinium, uranium, neptunium, plutonium, americium, curium, berkelium, californium, einsteinium, fermium, mendelevium, nobelium, and lawrencium, (II) alloys thereof, and (III) alloys containing one or more of such metals alloyed with an alloying component selected from the group consisting of magnesium, calcium, barium, strontium, cobalt and iridium.

The hydrogen-permeable material of the protective hydrogen-permeable barrier layer may suitably comprise a metal such as Pd, Pt, Ir, Mg, Ca, Ag, Au, Co, and alloys thereof. The rare earth metal thin film may in some instances be desirably overlaid by a hydrogen-permeable material that is doped with a dopant such as Mg, Ca, Al, Ir and/or Co.

As a further variation, the hydrogen-permeable protective overlayer may be formed of alternating doped and undoped material layers. The doped material layers may be formed of Pd, Ir and Pt, doped with a dopant species such as Mg and/or Al, and the undoped material layers may be formed of Pd, Ir and/or Pt.

The rare earth metal thin film devices of the invention may be employed for signal processing, including the steps of:

providing a rare earth metal thin film, contacting the rare earth metal thin film with hydrogen gas;

selectively imposing a predetermined voltage signal across the rare earth metal thin film, to selectively electrically switch the film between window and non-window states; and generating an output in response to which one of the states is present (transparent window or opaque non-window).

The rare earth thin films of the invention may be usefully employed in structural member selectively variable between window and non-window states, including a rare earth metal thin film, a source of hydrogen gas for contacting the rare earth metal thin film, and an electrical driver circuit which is selectively actuated to selectively impose a predetermined voltage signal across the rare earth metal thin film, to responsively place the rare earth metal thin film in a selected one of the window and non-window states.

As used herein, the term "window state" means optically transmissive, and the term "non-window state" means non-optically transmissive or optically opaque. The non-window state may for example be an optically reflective mirror state, or alternatively an optically opaque state.

As used herein, the term "thin films" will be understood as broadly referring to films having a thickness of less than about 1,000 microns.

In the use of rare earth metal thin films in the practice of the invention for applications such as hydrogen detectors, in applications in which the thin film will or may encounter oxidizing species in the environment being monitored for hydrogen, such as oxygen, moisture (relative humidity), nitrogen oxides, carbon oxides, etc., it is advantageous to coat or encapsulate the rare earth metal thin film with a hydrogen-permeable protective material that prevents such oxidizing species, as well as other deleterious species in the environment, from contacting the rare earth metal thin film.

The protective material may for example absorb oxygen and allow diffusion of hydrogen through the protective material to the rare earth metal thin film. Alternatively, the protective material may be impermeable to oxygen and/or other oxidizing species.

The protective material when present as an overlayer coating or encapsulant should be continuous and atomically dense in order to provide an effective barrier against oxidation. The thickness of the overlayer may be readily selected to minimize oxygen permeation while maximizing the response of the rare earth metal thin film to hydrogen.

In one embodiment of the present invention in which a protective material overlayer is employed, the overlayer may be formed of a metal such as Pd, Pt, Ir, or alloys or combinations thereof with one another or with other metal species. Particularly useful alloys for such protective material overlayers include Pd—Ag (20%) and Gd—Mg (30%).

The rare earth metal thin film may be formed by any suitable forming or deposition process. For example, the rare earth metal thin film may be formed by chemical vapor deposition, physical vapor deposition, solution deposition, electroplating, electroless plating, sputtering, or any other suitable technique or methodology for formation or deposition thereof. The rare earth metal film may be formed on any suitable substrate, e.g., silicon, silicon oxide, silicon carbide, alumina, vitreous or ceramic materials, etc.

A particularly preferred technique for forming the rare earth metal thin film in the broad practice of the present invention is chemical vapor deposition (CVD). Due to its high throughput and low cost, the CVD process is advantageous in fabricating sensor devices of the present invention in an efficient and economic manner. The ability of CVD to conformally coat substrates provides further benefit in the deposition of a protective overlayer material, in instances where the hydrogen sensor of the invention is fabricated with such a barrier material for preventing the reaction of the rare earth metal with oxidizing species in the environment being monitored for hydrogen.

The CVD process may utilize bubbler delivery or liquid delivery with subsequent flash vaporization, using a suitable rare earth metal precursor or source compound, to generate a precursor vapor which is transported to a heated substrate for decomposition to form the desired rare earth metal film. Such precursors must be robust and volatile at the temperature of vaporization, yet they must decompose cleanly and efficiently on the substrate. Particularly preferred precursors for rare earth metal thin film formation by CVD in the practice of the invention include tris(cyclopentadienyl) lanthanum, tris(cyclopentadienyl)yttrium, β-ketoamine complexes of lanthanum, β-ketoamine complexes of yttrium, β-diiminate complexes of lanthanum, β-diiminate complexes of yttrium; lanthanum amides, and yttrium amides.

Suitable precursors may be readily determined within the skill of the art by screening techniques conventionally used in the art of CVD formation of thin films, including thermogravimetric analysis (TGA) and differential scanning calorimetry (DSC) analysis.

For example, such simultaneous thermal analysis (STA) studies under Ar and vacuum may be conducted to screen candidate precursors for suitable thermal stability and transport properties.

The STA studies are suitably conducted under conditions simulating CVD conditions, e.g., under a flow of $H_2$ (5%) diluted with argon to provide data for predicting the major decomposition pathway(s) of the candidate precursors.

This combination of tests allows for rapid screening of a number of potential precursors, and also allows the study of the effect of other species present in the CVD process, e.g., reducing agents such as $NH_3$, on the decomposition pathway.

Various cyclopentadienyl $Cp'_3M$ complexes are well known for the chemical vapor deposition of metals such as La and Y. These complexes are readily synthesized by the reaction of metal halides with the desired sodium cyclopentadienyl salt. In the solid state these complexes exist as weakly associated polymeric chains which readily form adducts even with relatively weak donors such as tetrahydrofuran (THF).

Both $Cp'_3La$ and $Cp'_3Y$ sublime in vacuo at 200–250° C. Substitution on the Cp ring has a profound effect on the physical characteristics of these compounds. For instance, $Cp_3Y$ exists as an off-white solid at room temperature, while the butyl substituted $Cp'_3Y$ (i.e., $Cp'=C_4H_9C_5H_4$) exists as a yellow liquid. Various substituted cyclopentadienyl complexes of Y and La may therefore be synthesized and usefully employed in the broad practice of the invention. The substitutions on the cyclopentadienyl ($C_5H_4R$) ligands include R=Me, iPr, nBu along with substitution of the Cp by the indenyl ($C_9H_7$) ring.

Examples of indenyl precursor compositions include tris (indenyl)lanthanum and Y complexes. Due to the facile slippage of the indenyl ring between $h^5$ and $h^3$ states these complexes can provide highly suitable decomposition pathways to metal hydrides.

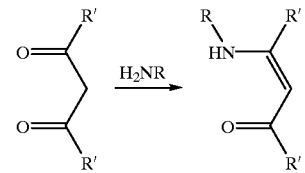

Once synthesized, the thermal transport and decomposition pathways of the specific rare earth metal precursor may be determined by TGA and DSC to determine its utility for forming the rare earth metal thin film of the present invention.

Beta-diketonate ligands may be advantageously employed in precursors such as $La(thd)_3$ as well as ligands such as β-ketoimines and β-diiminates.

The synthesis of β-ketoimines in instances where either R' or R" is not a bulky hydrocarbyl group may be carried out by condensation reaction between a primary amine and a β-diketone, to displace just one of the keto groups, as shown below:

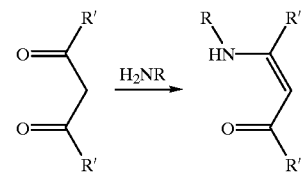

wherein R=–Me or –Ph

If the R' and R" groups are sterically larger than methyl or ethyl groups, an alternate pathway is required. As an example of such an alternative pathway, a trimethylsiloxyl intermediate may be employed, as in the synthesis of β-ketoimine illustrated below, wherein R=tert-Bu:

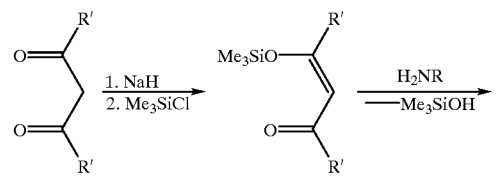

-continued

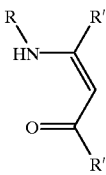

As a specific example of the foregoing, a rare earth metal complex may be synthesized by the reaction of M[N(SiMe3)2]3 (M=La, Y) with the β-ketoimine to yield the tris (ketoiminato)M complex, with the liberation of hexamethyldisilazane, which can be removed in vacuo.

Alternatively, β-diimine coordination chemistry may be employed for incorporation of two different substituents on each of the imino nitrogen atoms. This provides opportunity to further refine the steric and electronic characteristics of the complex near the metal center, and also influence the physical state (crystalline solid or liquid) of the product complex.

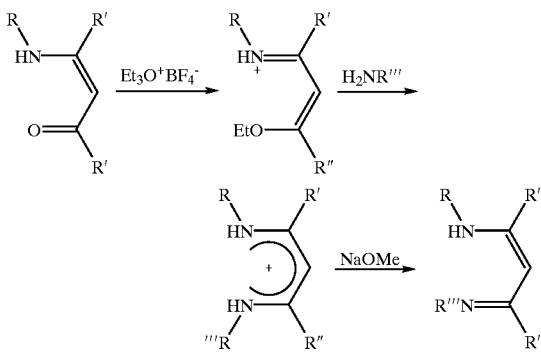

wherein R=R'''=-Me, tert-Bu and -Ph.

This route may for example be employed for diimines in which R=R'''=$CH_2CH_3$ and R'=R''=$CH_3$. Reaction of β-diimines with M[N(SiMe$_3$)$_2$]$_3$ (M=La, Y) yields the tris(diiminato)M complexes. One of the advantages of these complexes is the availability of a number of substituents (R, R', R'') that can be modified to selectively vary the volatility of the precursors.

Under a hydrogen atmosphere in chemical vapor deposition, the loss of the ligand of the foregoing precursors is "clean." Alternatively, metal nitrides can be further decomposed with the evolution of $NH_3$ either during deposition or in a post-deposition annealing step under $H_2$.

Lanthanum amides and yttrium amides are also effective precursors for thin film deposition in the rare earth metal thin films of the invention, due to their ability to form low coordination number complexes. The large cone angle of bulky amides such as —N(SiMe$_3$)$_2$ may be exploited in producing a coordination number of three, the lowest known for lanthanides.

Both La and Y amides are volatile. For instance, Y[N(SiMe$_3$)$_2$]$_3$ sublimes at 105° C. at $10^{-4}$ mm and is soluble even in nonpolar solvents. These characteristics make La and Y effective for use in liquid delivery systems for chemical vapor deposition. Y and La amides may be synthesized by the reaction of their chloride salts with an appropriate lithium amide. Examples of effective precursors for M(NR$_2$)$_3$ wherein R=SiMe$_3$, tert-Bu, Ph; an unsymmetrical amide (from a commercially available amine); and —N(Me)(tert-Bu).

Under the conditions used for chemical vapor deposition, the amide ligands decompose to yield amines and/or ammonia and volatile organic species.

La(hfac)$_3$(diglyme) is a suitable CVD precursor for La. La(hfac)$_3$ melts at 81° C., considerably lower than La(thd)$_3$, and undergoes vaporization at 175° C. at atmospheric pressure. The DSC of La(thd)$_3$ under argon, on the other hand, indicates a solid-solid phase change at 192° C. and a melting point of 260° C. La(thd)$_3$ begins vaporization at 225° C. with an extrapolated sublimation temperature of 280° C.

Unlike La(thd)$_3$, the sublimation of La(hfac)$_3$(diglyme) is unaffected by oxygen. Thus, while La(thd)$_3$ decomposes to La$_2$O$_3$ upon heating under oxygen La(hfac)$_3$(diglyme) sublimes intact. The marked chemical difference in the redox properties of La(hfac)$_3$(diglyme) makes it an effective precursor for the CVD of La metal films.

Y(NSiMe$_3$)$_3$ is a solid at room temperature and sublimes at 105° C. at $10^{-4}$ mm Hg. The vapor pressures of lanthanum amides are similar.

In the practice of the invention, wherein the rare earth metal thin film is intended to detect hydrogen in an environment potentially containing oxidizing species reactive with the rare earth metal thin film, an overlayer coating may be employed to protect the rare earth metal from reaction with the oxidizing species.

The rare earth material thin films are preferably as thin as practical since thin films require lower hydrogen exposure to change optically.

For example, preferred rare earth material thin films are from about 50 to about 2000 nm thick, more preferably from about 50 to about 200 nm thick, with a protective layer having a thickness of from about 2 to about 1000 nm, and more preferably fom about 2 to about 100 nm, e.g., a 20 nm thick, protective layer of a material such as Pd on a rare earth metal thin film of 100 nm thickness. The overlayer is preferably thick enough to adequately protect the sensor from oxidation and thin enough to leave unchanged the optical properties of the device.

The protective overlayer may be deposited for formed over the rare earth metal thin film in any suitable manner, including spraying, solution deposition, dipping, chemical vapor deposition, physical vapor deposition, focused ion beam deposition, sputtering, etc. Generally, the methods described hereinabove for formation or coating of the rare earth metal thin film in the first instance may also be used for forming the protective overlayer thereon, and vice versa.

The protective overlayer may be formed of any suitable material of construction, which is suitably effective to prevent chemical reaction or sorption processes from occurring that would preclude the efficacy of the rare earth metal thin film for hydrogen sensing.

Although the overlayer material is typically in the form of a film that is formed directly on the underlying rare earth metal thin film, it is possible within the broad scope of the present invention to utilize a protective material such as a free-standing film or a membrane that is in spaced relationship to the rare earth metal thin film.

For example, the protective material may comprise a membrane that is permselective for hydrogen only. The membrane may thus form a cell within which the rare earth metal thin film is deployed.

The protective overlayer material may for example be a metal, a polymeric film material, a vitreous or ceramic material, etc. Examples of useful metals include Pd and other noble metals such as Pt, Ir, etc.

In the preferred practice of the invention, Pd is utilized as a protective overlayer material, and may be usefully deposited on the rare earth metal thin film by chemical vapor deposition from a corresponding precursor.

Examples of precursors that may be used as source compositions for deposition of Pd by CVD include Pd(hfac)$_2$, Pd(allyl)$_2$ and CpPd(allyl).

The $^1$H NMR of Pd(hfac)$_2$ shows a single resonance at 5.88 ppm. The DSC of the compound reveals a sharp melting at 103.7° C. followed by an endotherm, indicating vaporization, at 166.2° C. The TGA trace reveals complete vaporization by 175° C., making this an effective precursor for the deposition of a protective palladium metal overcoat.

If in the use of Pd(hfac)$_2$ as a precursor for Pd deposition, fluorine incorporation into the film is in excess of the level desired in the product Pd film, an alternative precursor such as Pd(allyl)2 or CpPd(allyl) can be employed.

By way of specific example, optimal film growth conditions in the CVD reactor for the formation of the Pd overlayer, in one specific embodiment of the invention, wherein argon and hydrogen are utilized as carrier gases and the Pd precursor composition was volatilized and flowed through a precursor manifold to a chemical vapor deposition reactor for deposition of Pd on the substrate, were as follows:

Substrate temperature: 590° C.
Substrate type: Fused quartz
Total reactor pressure: 2 Torr
Reactor wall temperature: >200° C.
Ar flow (through precursor manifold): 100 sccm
H$_2$ flow 450 sccm All gases used in depositing the Pd are preferably ultra high purity (UHP) grade. In determining optimum values for the concentration of H$_2$ and the substrate temperature in a specific application of the invention, it may be useful to conduct test runs in which these process parameters are iteratively varied, and the resulting films evaluated, to select the optimum values for such specific application.

In a preferred aspect of the invention, the thickness of a Pd or other noble metal overlayer is selected to optimize the response of the films to hydrogen. The overlayer is desirably continuous and atomically dense in order to provide an effective barrier against oxygen. The thickness of the protective layer is strongly dependent on the average roughness of the underlying film. The smoother the topography of the underlying rare earth metal, the thinner the overlayer can be to provide effective coverage.

Pd absorbs approximately nine hundred times its volume of hydrogen gas. Although such absorption is reversible and highly selective for hydrogen, excessive dissolution of hydrogen in the Pd overlayer may slow its diffusion to the underlying rare earth metal thin film. Such hydrogen dissolution may also result in slow "re-zeroing" of the sensor after detection of hydrogen, due to slow rates of desorption.

Both Pt and Ir absorb hydrogen and allow hydrogen to diffuse through them and can readily be used in place of Pd. A number of Pd-rich alloys also absorb hydrogen, e.g., Pd—Ag (20%). Membranes of this alloy do not undergo the volume expansion and cracking that is sometimes observed for pure Pd and that may limit the use of such pure material. Pd-rich alloy membranes are used industrially and may be advantageously employed in the broad practice of the present invention.

Rare earth metal alloys of magnesium are also useful as protective overlayer species. The overall hydrogen gas transmission rate of a rare earth-magnesium alloy hydride is higher than that of the pure metal hydride. The heat of formation of magnesium hydride (−33 kJ/mol H) is similar to that of rare earth hydrides (c.a. ~40 kJ/mol H) and the uptake of hydrogen by these alloys is reversible. In addition, the band gap of magnesium hydride is large enough that it forms a transparent hydride.

Alloying Gd with Mg to form an overlayer material yields a number of benefits. The alloyed films display much higher transmittance than pure Gd films. In Gd—Mg (30%) alloys maximum transmittance is achieved at pressures well below 0.1 bar. This characteristic makes the alloyed film very sensitive to hydrogen. The slope of total transmittance vs. P[H$_2$] curve, below 1 bar, changes considerably with the concentration of Mg in the film. Alloying with a suitable metal, therefore, permits the sensory response of the film to be selectively "engineered" for specific concentrations of hydrogen in the product sensor device.

Alloying also increases the transmission ratio (i.e., transmission of hydrided film/transmission of dehydrogenated film) to over 3000. This is due to the virtual elimination of all residual transmission in the visible window. Residual transmission is typically small (c.a. 1.5%) and of indeterminate origin. It is observed when samples exposed to hydrogen are allowed to desorb in air. Alloying with magnesium shifts the transmission window to shorter wavelengths while gradually reducing the % transmission. For Gd—Mg alloy films containing 30 at. % Mg, the maximum transmission of a 200 nm layer is 0.01%. These properties make the Gd—Mg composition useful as an overlayer material to form a highly sensitive thin film sensor.

Alloys containing Mg at concentrations higher than 50 at. % exhibit three different optical states: transparent, absorbing, and reflecting; rather than just transparent and reflecting. This observation can be exploited to provide another intermediate sensory response, and enables the use of such alloys in tri-state optical switches.

The foregoing examples point up the utility of engineering the band gap and free energy of the rare earth dihydride to trihydride transition, and such modification may be effected in the broad practice of the invention by the addition to the overlayer film of a wide variety of potentially suitable dopants.

The specific dopant employed, and its concentration, are appropriately selected to enable the formation of an alloy hydride that has a band gap large enough to be transparent in the visible region. Ideally, the dopant will also render the dihydride to trihydride equilibrium thermodynamically neutral. Mg, Ca, Al, Ir and Co are potentially useful dopant species for such purpose. Transition metal elements such as Co and Ir form a variety of stoichiometric and non-stoichiometric hydride species and may be particularly useful in a given end use application.

In one embodiment of the invention, the overlayer on the rare earth metal thin film may be layered, with alternating constituent layers of barrier material and doped layers, as another technique for selectively varying the response characteristics of the overlayer to achieve a desired sensory sensitivity for the rare earth metal thin film sensor.

For example, a sensory Y and/or Gd film may be formed with alternating layers of barrier such as Pd, Ir or Pt or dopants such as Mg or Al, to provide maximum sensitivity and capability over a wide range of hydrogen concentration. The Pd/Pt interlayers in such a structure act as hydrogen storage layers as well as oxygen barrier layers, thereby enhancing the sensitivity of the film. Such a construction also allows reduction of the thickness of the top layer well below 50 Å.

The foregoing illustrative materials, Pd, Ir, Pt, Mg, and Al, may be deposited to form the sensor device by any suitable method, with CVD being generally preferred. A wide variety of useful precursors for such CVD formation of the material on a given substrate or intermediate structure of the sensor may be readily determined within the skill of the art and without undue experimentation.

Examples of potentially useful precursors for Mg and Ir include Mg(thd)$_2$ and (COD)Ir(hfac), respectively.

Precursors for Al include, for example, the dimethylethyl amine adduct of alane ($AlH_3$) or aluminumhydride (DMAH), an air sensitive volatile liquid that is useful to deposit high quality aluminum films.

Cobalt precursors include cobalt beta-diketonates such as $Co(thd)_2$ or $Co(hfac)_2$.

Referring now to the drawings, FIG. 1 is a schematic representation of a hydrogen sensor 10 according to one embodiment of the invention, in a non-hydrogen environment.

The sensor 10 includes a substrate 12 with a top substrate surface 14 receiving a light beam 20 impinged thereon from a focusing head 22 joined by optical fiber 24 to light generation unit 26. The light generation unit 26 is powered by means of a power line 28 connected to the central processor unit 30, which may comprise microprocessor or computer control elements for actuation, monitoring and control of the hydrogen sensor apparatus.

The sensor 10 further comprises a rare earth metal thin film 16 on the substrate, with the rare earth metal thin film 16 being overlaid by a palladium thin film 18 which serves to prevent oxygen and other oxidizing species from contacting the rare earth metal thin film.

In the system as shown in FIG. 1, the sensor 10 is disposed in a non-hydrogen environment, and the rare earth metal thin film is therefore correspondingly optically non-transmissive and is in a reflective state. The palladium overlayer 18 optionally has been previously contacted with hydrogen in sufficient concentration to absorb hydrogen therein and constitute the rare earth metal thin film as a divalent rare earth metal hydride film.

It will be recognized that the rare earth metal film may be formed and maintained as a pure elemental metal film, or alternatively, the metal film may be prereacted with sufficient hydrogen to convert the metal film to a metal dihydride film.

The impinged light beam 20 therefore is reflected from the sensor 10 to the detector 34 on the detector head 36. The detector head 36 may comprise a charge coupled device or photosensor which transmits a signal indicative of the reflected light beam to the central processor unit 30 through the optical fiber array 32. The central processor unit then processes the signal carried by the optical fiber array 32, and produces an output indicative of the absence of hydrogen in the environment to which the sensor is exposed.

Figure 2:
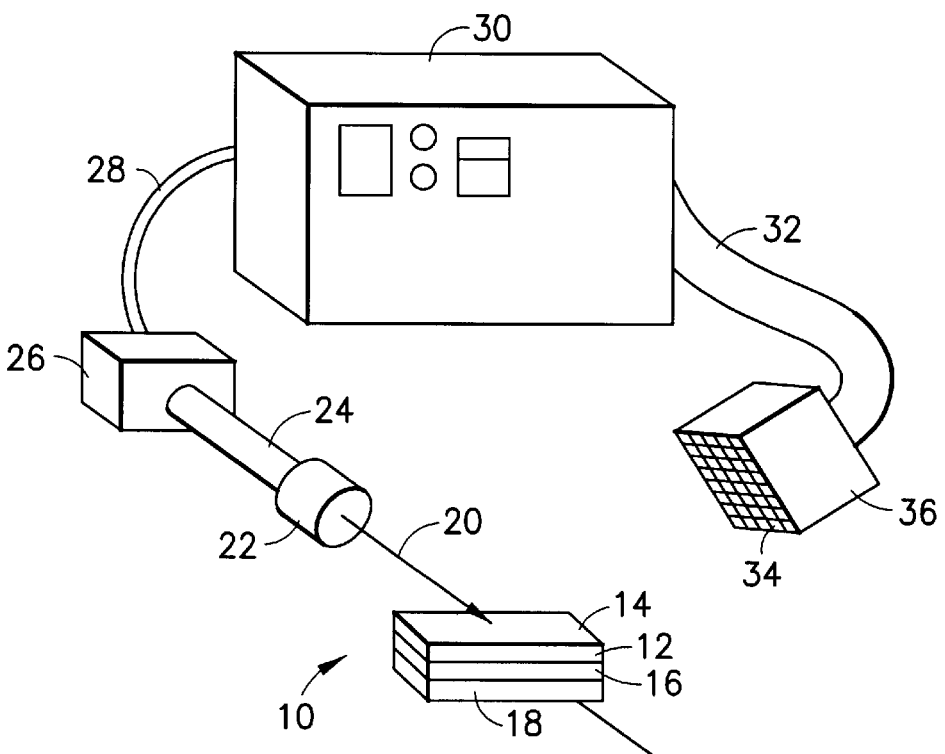
FIG. 2 is a schematic representation of the hydrogen sensor of FIG. 1, in exposure to hydrogen in the environment of the sensor element.

FIG. 2 is a schematic representation of the hydrogen sensor 10 of FIG. 1, in exposure to hydrogen in the environment of the sensor element. All of the parts and features of FIG. 2 are numbered correspondingly with respect to the same parts and features of the FIG. 1 drawing.

As a result of hydrogen being present in the environment being monitored by the sensor, the rare earth metal-based thin film 16 is converted from an optically non-transmissive state to an optically transmissive state, in which the light beam is passed through the rare earth metal film, and does not reflect to the detector. The detector upon failing to receive a reflected light beam then actuates the central processor unit to indicate the presence of hydrogen in the environment being monitored by the hydrogen sensor.

The output of the central processor unit 30 may include any perceivable output, such as auditory output, visual output, tactile output (as for example when the hydrogen sensor is adapted to be worn on the body of a user, and the central processor unit comprises a vibrator imparting vibratory sensation to the user's body when hydrogen is detected in the environment, such as may be useful in environments where auditory or visual outputs are not readily perceivable), etc.

In lieu of producing an output which is perceivable, the central processor unit 30 may be programmed to actuate means for eliminating hydrogen from the environment being monitored, as for example a sweep gas flushing operation to purge the environment of the hydrogen gas.

It will be recognized that the hydrogen sensor may be constructed so that the rare earth metal thin film is arranged in hydrogen permeation exposure to the environment being monitored. For example, the face of the sensor defined by the bottom surface of the palladium layer in the FIGS. 1 and 2 drawings may be contained in a sensing head which is insertable into a specific gas environment susceptible to the incursion or in situ generation of hydrogen therein.

Figure 3:
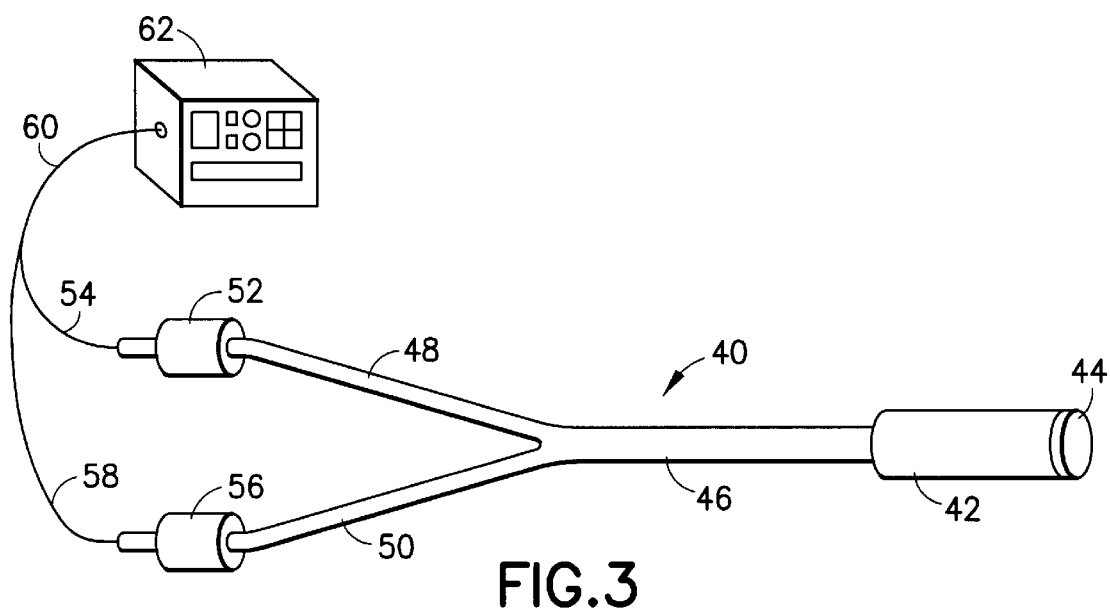
FIG. 3 is a schematic representation of a remote hydrogen sensor monitored by a miniature fiber optic according to another embodiment of the invention.

FIG. 3 is a schematic representation of a miniature fiber optic hydrogen sensor 40 according to another embodiment of the invention. The fiber optic sensor 40 includes a silicon housing 42 on the distal end of which is provided a rare earth hydride sensory film 44 joined in light transmissive relationship with a cladded optical fiber 46. The cladded optical fiber 46 at its proximal end splits into two branches 48 and 50 as shown.

The optical fiber branch 48 is coupled to a light emitting diode 52. The LED 52 in turn is joined by signal transmission branch line 54 to main signal transmission line 60. The optical fiber branch 50 is coupled to a photodiode 56 which in turn is joined by signal transmission branch line 58 to the main signal transmission line 60.

The main signal transmission line 60 is connected to the central processor unit 62. The central processor unit 62 serves to actuate the light emitting diode 52 to emit light carried by the branch 48 of the optical fiber to the main transmission portion of the cladded optical fiber 46. The light beam transmitted by the fiber 46 then is guided to the rare earth hydride sensory film 44.

If the film 44 is exposed to hydrogen in the gas environment being monitored, then the light is not reflected back down the cladded optical fiber 46 in the reverse direction, as is the case when the film 44 does not encounter hydrogen. The absence of reflected light reaching the photodiode then results in a corresponding signal being sent from the photodiode to the branch line 58 and main signal transmission line 60 to the central processor unit 62, which results in the central processor unit 62 outputting an output indicative of the presence of hydrogen in the gas environment being monitored by the device.

In operation, when hydrogen is not encountered in the gas environment, the incident light beam on the film 44 is reflected through branch 50 of the optical fiber. The photodiode 56 then produces a correlative signal passed in branch line 58 to the main signal transmission line 60 from which it is passed to the CPU 62, which maintains an appropriate monitoring status indicative of the absence of hydrogen gas in the environment being monitored.

Figure 4:
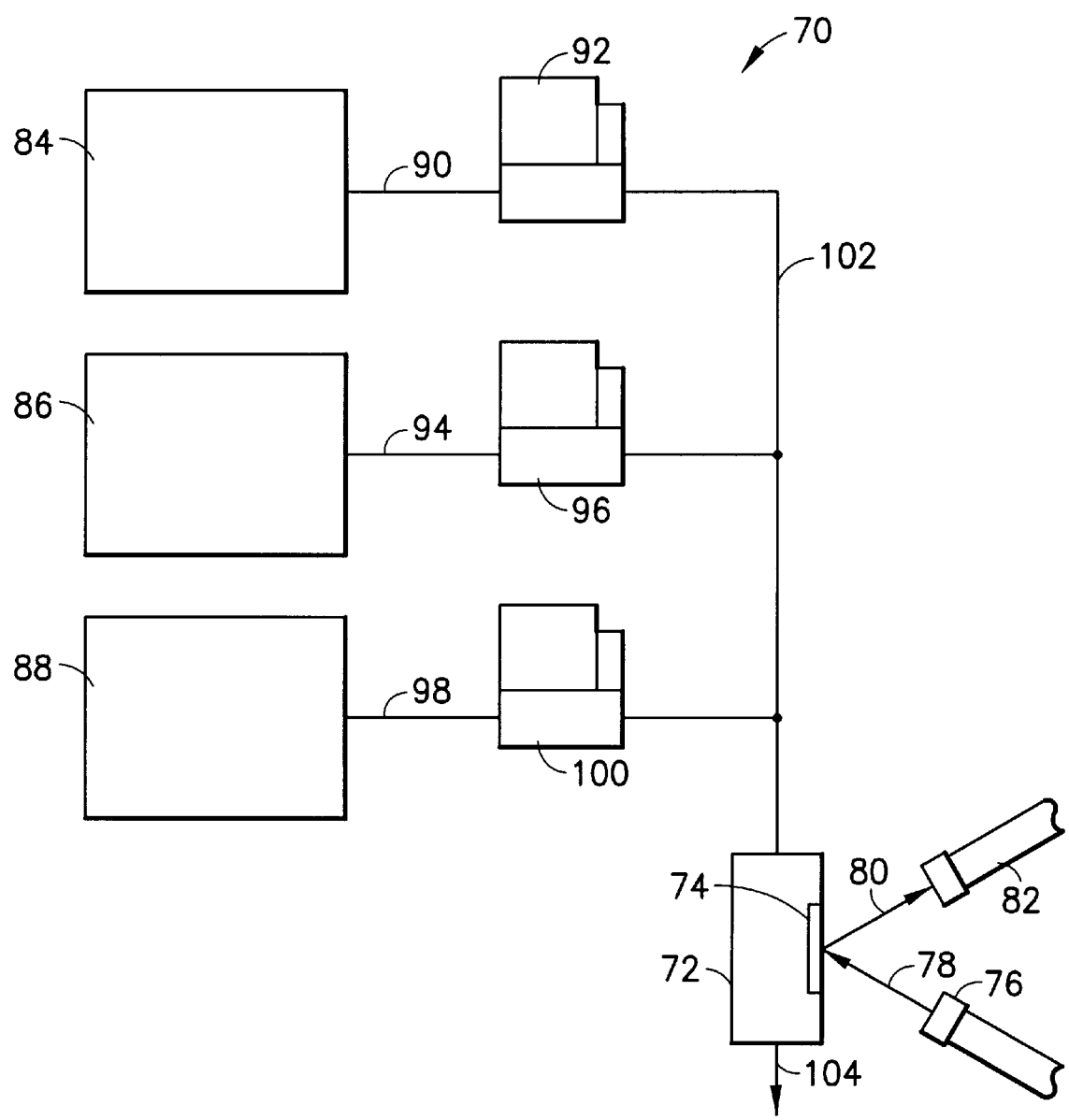
FIG. 4 is a schematic representation of an optical test bench system for evaluation of thin films.

FIG. 4 is a schematic representation of an optical test bench system 70 for evaluation of thin films.

The system shown in FIG. 4 includes a filtered light source 76 producing the filtered light beam 78 and a photodetector 82 receiving the reflected light 80 indicative of the absence of hydrogen in the cell 72. The bench may for example be equipped with a He—Ne laser and a He—Ne photodiode to accurately measure the optical transparency of rare earth metal films under varying concentrations of hydrogen.

The system 70 includes a wet air or nitrogen source vessel 84 joined by line 90, containing mass flow controller 92 therein, to the manifold line 102 joined in gas flow communication with the optically transparent cell 72 having rare earth metal film 74 therein. Also joined to the manifold line 102 by means of line 94 having mass flow controller 96 therein is a dry air or nitrogen source vessel 86, and a hydrogen source vessel 88 is joined by line 98 having mass flow controller 100 therein to the manifold line. The gas flowed into the cell 72 is exhausted therefrom in discharge line 104.

Hydrogen from source vessel 88, diluted in a mixture of air from source vessels 84 and/or 86, is fed to the optically transparent cell 72, to allow simultaneous measurement of the resistance as well as the optical transmittance of the film as a function of hydrogen concentration. Both reflectance spectra and transmittance spectra can be recorded on the optical bench.

The optical bench system 70 allows accurate measurement of the state of the film in the optically transparent cell 72, under conditions of various mixtures of gases, and permits the empirical selection of light emitting diodes or other light beam sources of appropriate wavelength for a given end use application with a specific rare earth metal thin film hydrogen detector element.

Figure 5:
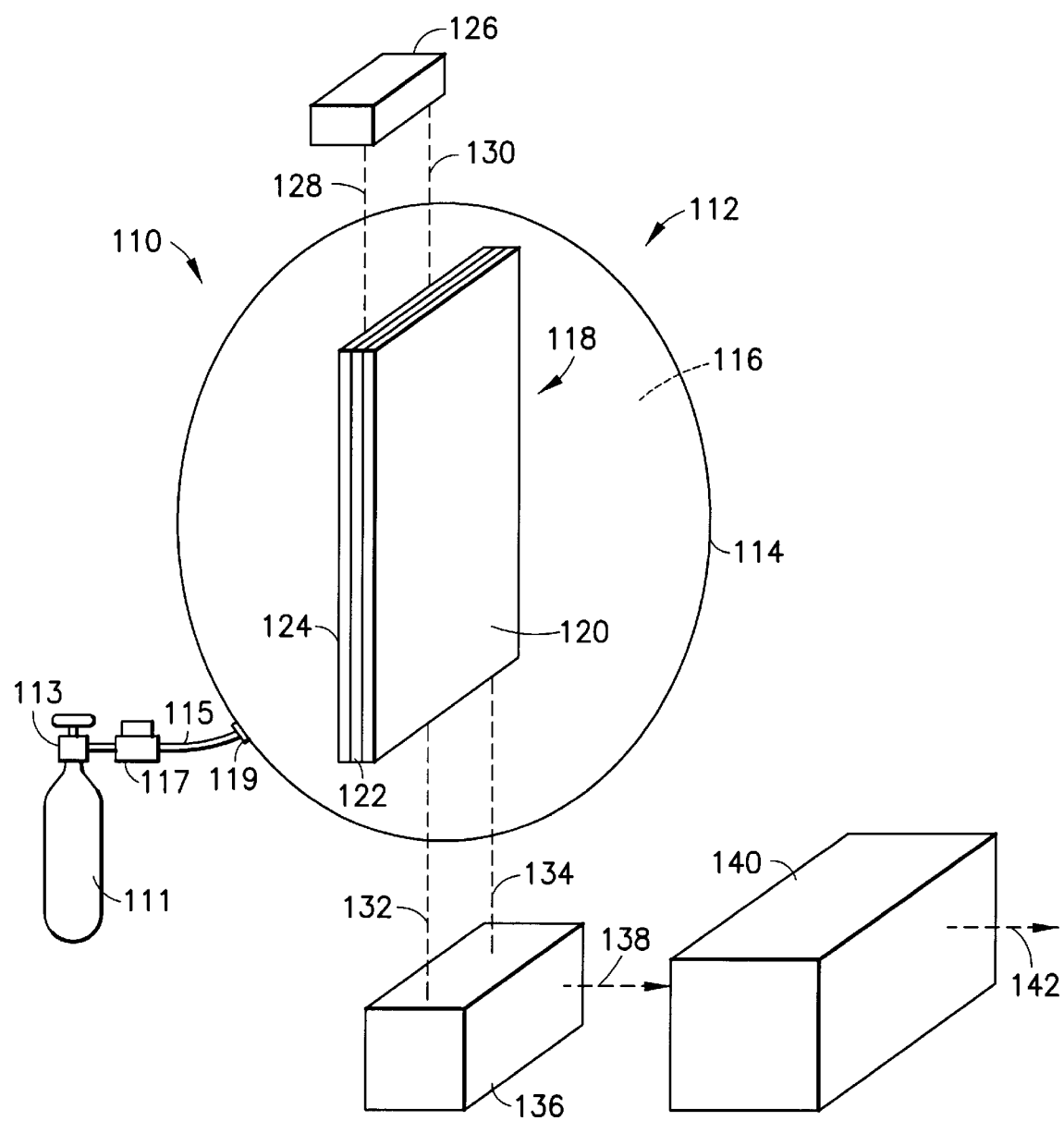
FIG. 5 is a schematic representation of a signal processing assembly according to another embodiment of the invention.

FIG. 5 is a schematic representation of a signal processing assembly 110 according to another embodiment of the invention.

In the FIG. 5 system, a controlled microenvironment chamber 112 is provided, as bounded by a glass (or other transparent material) globe 114 defining therewithin an enclosed interior volume 116.

The globe 114 is coupled in gas supply relationship with a cylinder 111 of hydrogen gas. The cylinder 111 is provided with a valve head 113 joined to gas flow conduit 115 having flow control pump 117 therein. At its outer end, the gas flow conduit 115 is joined by means of coupling 119 to the globe 114, so as to selectively flow hydrogen gas into the interior volume 116 of the globe when the valve of the valve head 113 and the flow control pump 117 are selectively correspondingly actuated for such purpose.

A hydrogen sensitive film element 118 is disposed in the interior volume of the globe 114. The film element 118 comprises a substrate 120 on which has been deposited a film 122 of a rare earth metal such as those illustratively mentioned hereinearlier. The film 122 of the rare earth metal in turn is overlaid by an oxygen barrier film 124 that is permeable to hydrogen gas.

An electrical power supply 126 may be provided which is joined by electrical leads 128 and 130 to the film element 118 as shown, for impressing a selected voltage on the film element, or otherwise imparting a desired electrical input to the film element.

An electrical resistivity monitor 136 is joined by leads 132 and 134 to the film element 118, to monitor the change in electrical resistivity of the film element incident to the introduction of hydrogen to the interior volume of the globe 114 from cylinder 113.

By this arrangement, hydrogen may be selectively introduced to the interior volume of the globe by actuation of valve head 113 valve means and flow control pump 117 in order to induce a physical property change in the resistivity of the film element, and such change then is sensed by the monitor 136. The monitor 136 then responsively generates a correlative signal 138 which is transmitted to signal processing unit 140, to generate an output signal 142.

To induce a change of state of the film element, the flow control pump 117 may be actuated to withdraw hydrogen gas from the interior volume 116 of the globe, and/or the voltage impressed by power supply 126 may be varied, so that the rare earth metal thin film in the film element 118 is changed back from a semiconducting transparent state to the original opaque metal state. The change of state is sensed by the monitor 136. The monitor 136 then responsively generates a correlative signal 138 which is transmitted to signal processing unit 140, to generate an output signal 142.

Since the FIG. 5 system effectuates a selective switching of the film element between semiconducting transparent and metal conducting opaque forms of the film element, it is apparent that the system may be employed as an optical router switch device, when a light beam is impinged on the film element, with suitable photogenerating and photodetecting means being operatively associated therewith.

Figure 6:
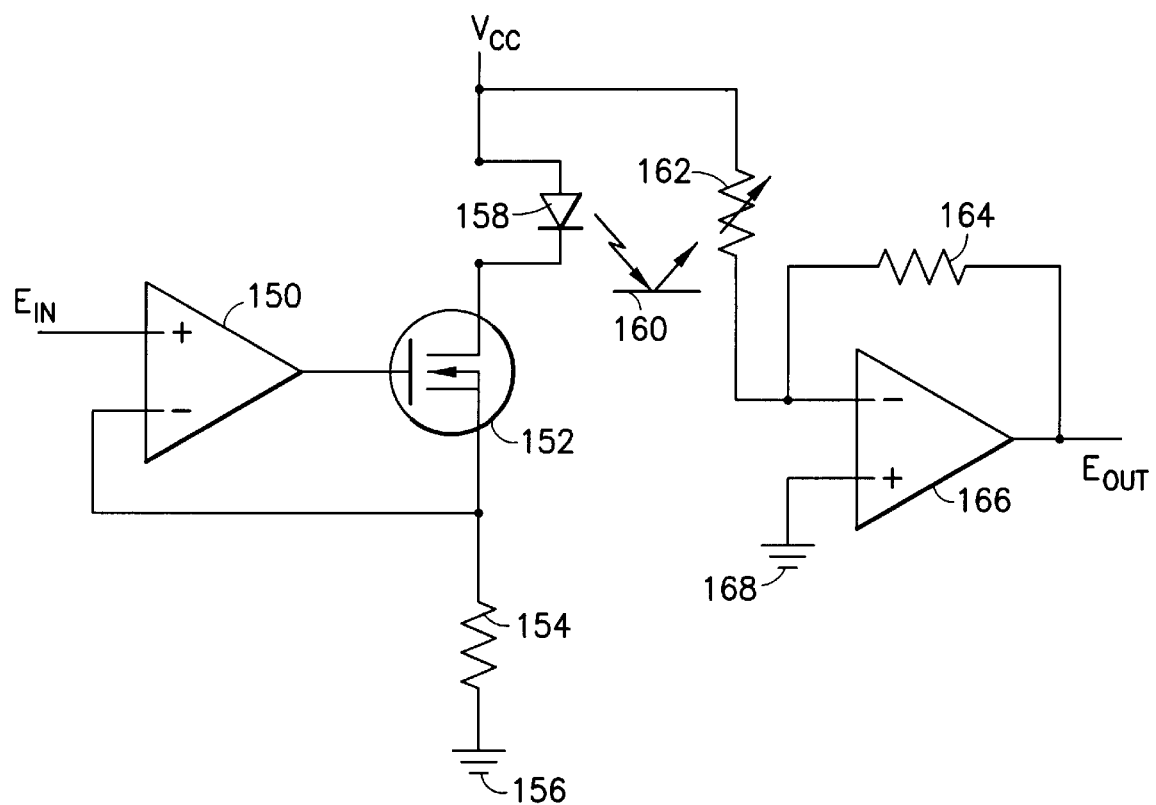
FIG. 6 is a circuit diagram for an electrical driver for a rare earth metal thin film device according to another aspect of the invention.

FIG. 6 is a circuit diagram for an electrical driver for a rare earth metal thin film device according to another aspect of the invention.

FIG. 6 depicts an illustrative circuit for driving an LED and photo-detector (in this case a photo-resistor) circuit, such as may be employed in connection with a rare earth metal thin film sensor 160 of the present invention. The circuit includes resistors 154 and 164, photoresistor 162, rare earth thin film 160, operational amps 150 and 166, and grounds 156 and 168. A fixed $E_{in}$ is applied at the first transistor. The output of operational amplifier (opamp) 150 is fed to a n-channel MOSFET 152. The MOSFET becomes conductive. The current is increased until the voltage drop across the power resistor is equal to $E_{in}$. Hence this circuit drives the LED 158 at constant current. This current is equal to $E_{in}/200$ Ω. By varying $E_{in}$, the LED 158 can be driven at different and known values.

The receiver is driven at $V_{cc}$. Since the resistance changes with changes in the impinging light, the current flowing through the photoresistor 162 will change. The voltage output of the opamp on the left will follow the changes in the resistance of the photoresistor 162. It may be necessary for reasons of speed or sensitivity to switch to a photodiode or phototransistor.

The driving circuits for the photodetectors are very similar. For example, such a photodetector can be constructed using the following specifications:

approximate size of device=1×2×4 inches.

weight<<1 lb.

power requirements of 9–24 VDC @500 mA.

analog output ($H_2$ concentration) of 4–20 mA.

two relay alarm points (sensor/device failure and [$H_2$] above a set point)

RS232 line with appropriate data

One preferred embodiment of the present invention comprises a hydrogen sensor that is capable of exclusively detecting hydrogen in a device with zero electrical charge at the sensor head. The sensor head, consisting of a housing containing a diffusion barrier, such as a palladium thin film, and the yttrium thin film sensor element, is coupled by a fiber optic cable to a remote optical sensing device which delivers a light source across the yttrium thin film and collects resultant reflected light from the thin film.

The yttrium thin film possesses the ability to reflect light in the absence of hydrogen (opacity) and to transmit light in the presence of hydrogen (transparency). This sensor is also capable, by incorporating a light source and a sensitive photo-detector, of detecting various levels of hydrogen, thus providing a broad range of detectability.

Figure 7:
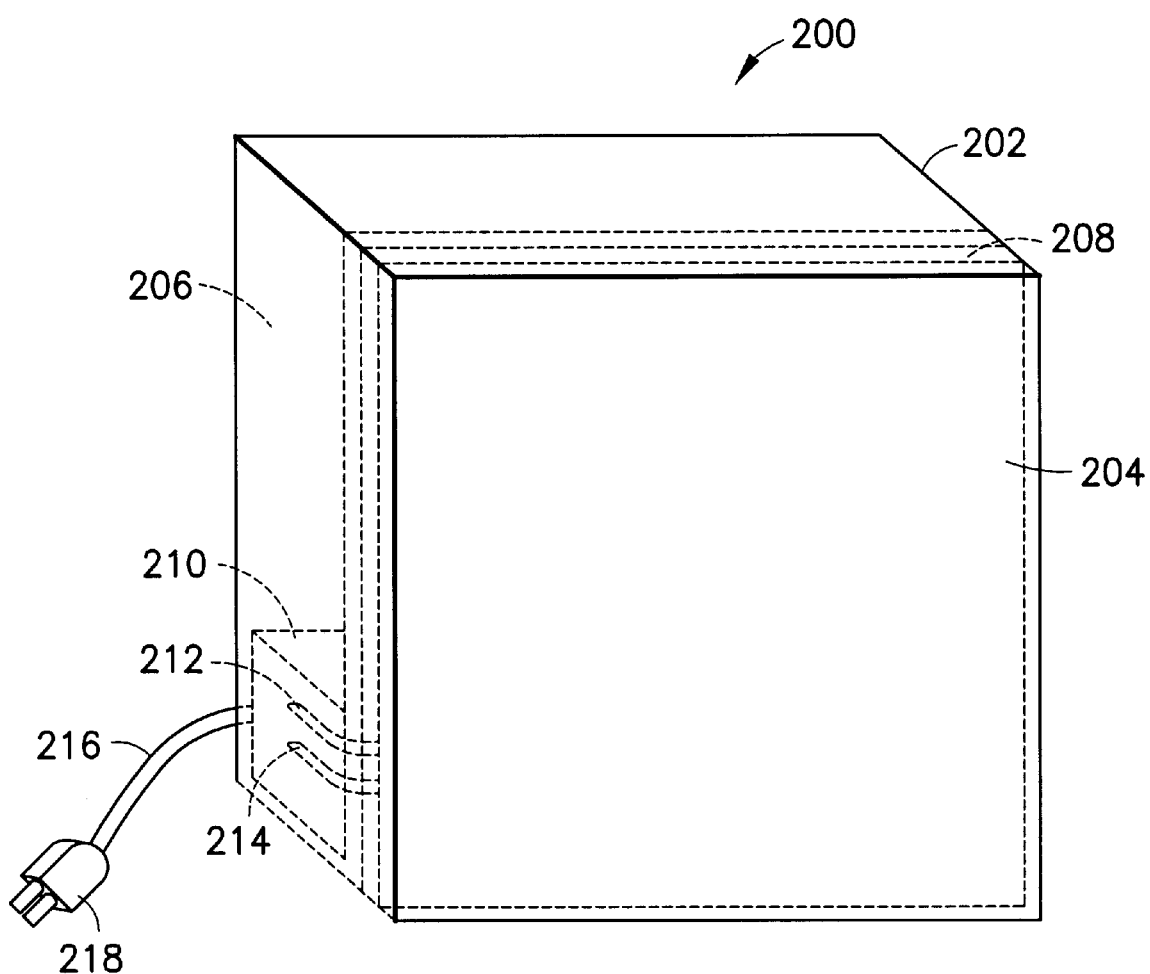
FIG. 7 is a perspective view of a structural window element according to yet another embodiment of the invention.

FIG. 7 is a perspective view of a window structure 200 according to yet another embodiment of the invention. The window structure comprises a casing 202 having a transparent front face 204 and enclosing an interior volume 206 holding the thin film element 208.

In this embodiment, the thin film element 208 including the active rare earth metal sandwiched between a quartz substrate and a palladium protective layer, is positioned against a transparent panel at the face of the window structure.

The interior volume 206 of the window structure 200 also has a hydrogen gas source and processor unit 210 therein which is coupled by means of leads 212 and 214 to the thin film element 208. The hydrogen gas source and processor unit 210 is powered by means of electrical line 216 having an outlet plug 218 at its proximal end, for engagement with an electrical receptacle, to power the system.

In operation, the window structure is selectively placed in a desired one of window (optically transmissive) and opacified (optically non-transmissive) states.

The system, once powered by engaging the plug 218 with an electrical outlet receptacle, may be switched on to a window state thereby actuating the hydrogen gas source and processor unit 210 to emit hydrogen gas into the interior volume 206 into contact with the thin film element 208, thereby causing the rare earth film of the thin film element to convert to a trihydride form and to exhibit transparency.

When the user thereafter wants to induce an opacified state, the system may be switched to an opacified setting, thereby actuating the hydrogen gas source and processor unit 210 to take up hydrogen gas from the interior volume 206, e.g., by adsorbing the hydrogen gas on a sorbent material selective therefor in the hydrogen gas source and processor unit 210. With the withdrawal of hydrogen from the thin film element, the element becomes opacified.

In the absence of hydrogen, the sensory film is reflective and reflects light.

In the presence of hydrogen, the sensory film becomes increasingly transparent.

The user therefore is able to selectively induce a window state or a mirror state. The window structure is therefore amenable to a wide variety of uses, as windows, screens, security shades, etc.

Figure 8:
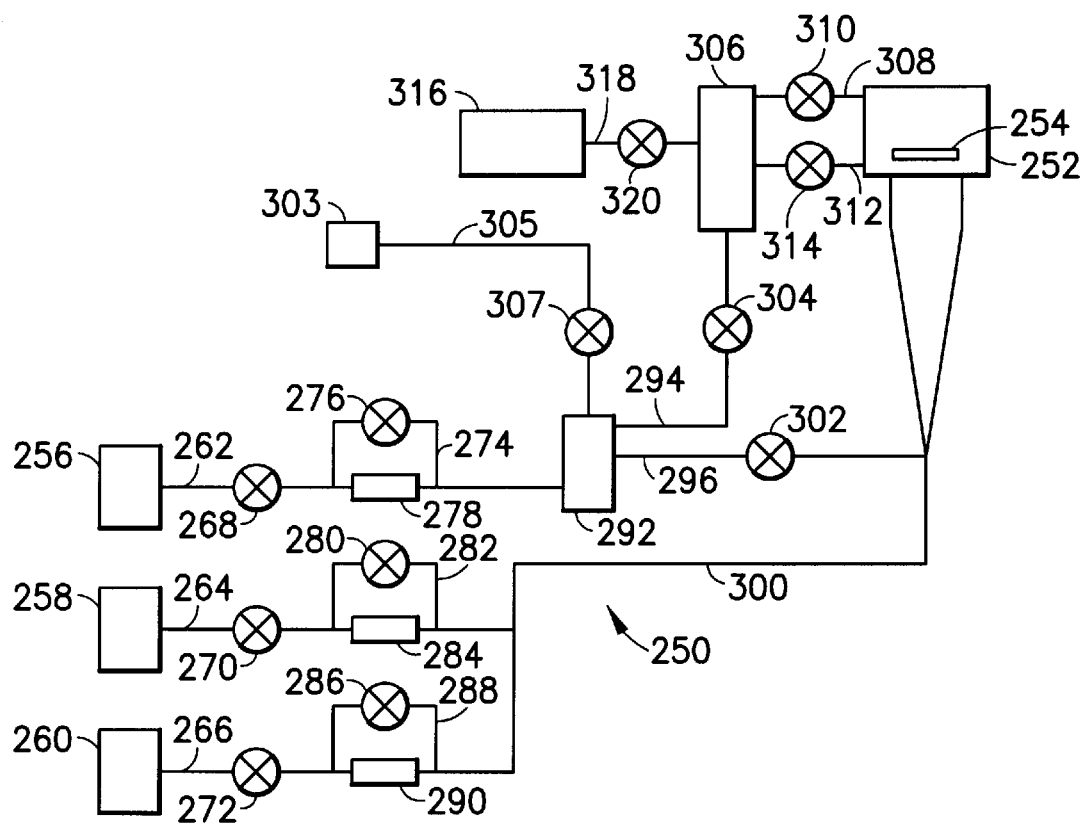
FIG. 8 is a schematic representation of a thermal MOCVD reactor system for film growth for forming rare earth metal thin film hydrogen sensor devices in accordance with one embodiment of the present invention.

FIG. 8 is a schematic representation of a thermal MOCVD reactor system 250 for film growth for foimsing rare earth metal thin film hydrogen sensor devices in accordance with one embodiment of the present invention.

The process system shown in FIG. 8 utilizes a chemical vapor deposition reactor 252 in an inverted vertical configuration. The substrate susceptor 254 holds a wafer (not shown). The vessel 252 is made of fused quartz and has cylindrical geometry. The walls of the reactor may be heated to prevent condensation of the precursors.

Individual reagents are delivered using separate liquid reservoirs (not shown). The metalorganic precursors can be delivered either as solutions or as neat liquids. Liquid delivery of precursor may be advantageously employed, in which the reagent is provided in a liquid which is pumped by the liquid pump 303 in line 305 having flow control valve 307 therein to the flash vaporization chamber 292.

In the flash vaporization chamber, the precursor liquid is flash vaporized to yield the precursor vapor for the deposition of the desired material. The resulting vapor flows in line 296 having flow control valve 302 therein, to the reactor 252.

Argon carrier gas from source vessel 256 is flowed in line 262 having flow control valve 268 therein to the vaporization chamber 292. Line 262 contains mass flow controller 278, and a bypass line 274 containing bypass flow control valve 276.

Hydrogen gas from source vessel 258 is flowed in line 264 having flow control valve 270 therein to manifold line 300.

From manifold line 300 the gas stream containing hydrogen is flowed into the reactor 252. Line 264 contains mass flow controller 284, and a bypass line 282 containing bypass flow control valve 280.

Likewise, argon or an optional co-reductant species from source vessel 260 is flowed in line 266 having flow control valve 272 therein to the manifold line 300. Line 266 contains mass flow controller 290, and a bypass line 288 containing bypass flow control valve 286.

The reactor 252 is exhausted by means of pump 316, joined by line 318 having throttle valve 320 therein to the trap 306. The trap 306 in turn is joined to the reactor by means of line 308 containing flow control valve 310 therein, and line 312 containing flow control valve 314 therein.

The trap 306 is coupled via line 294 containing valve 304 to the vaporization chamber 292.

The system shown in FIG. 8 may be advantageously used to form thin film elements for sensors in the broad practice of the present invention.

Figure 9:
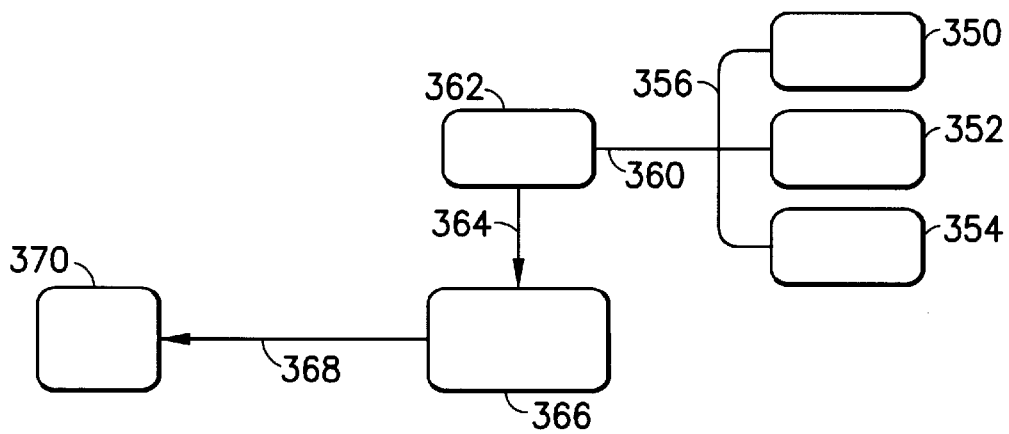
FIG. 9 is a schematic representation of a liquid delivery system for controlled introduction of metalorganic compounds to a CVD reactor.

FIG. 9 is a schematic representation of a liquid delivery system for controlled introduction of metalorganic compounds to a CVD reactor.

In the FIG. 9 system, precursor liquids are supplied from respective liquid reservoirs 350, 352 and 354 to a manifold 356 from which the selected reagents dispensed to the manifold are flowed in line 360 to the liquid pump 362. The liquid pump 362 pumps the supplied precursor liquid in line 364 to the vaporization zone 366.

The resulting precursor vapor is flowed in line 368 to the CVD reactor 370 for deposition of the desired thin film material. For example, the reservoirs may comprise a precursor for lanthanum, which is dispensed, flash vaporized and contacted with the substrate in the CVD reactor to form a film of lanthanum on the substrate.

After the deposition of lanthanum, the reactor may be purged, e.g., with hydrogen, and then Pd or other overlayer film may be deposited from a suitable Pd precursor supplied from the Pd reservoir.

A significant advantage of the liquid delivery approach is that organometallic precursors are kept at ambient temperatures until just before vaporization. This greatly reduces the thermal decomposition of the precursors and allows for the transport of relatively thermally sensitive precursors. Downstream of the vaporization zone the precursors flow to the reactor. This part of the system must be heated to prevent condensation of the reactants.

Film growth by physical vapor deposition (PVD) may be advantageously carried out using any of various commercially available evaporation systems, e.g., an Airco Temescal multi-crucible, single gun, e-beam evaporation system. With the aid of a cryopump, a base vacuum of $10^{-7}$ Torr can be established in such system before commencing operation. Residual oxygen and water may be scavenged from the evaporation chamber of the system, prior to deposition, by heating a target in the system, such as a titanium target, by e-beam.

Such heating further reduces the base pressure to suitably low levels, e.g., well below $10^{-8}$ Torr. The system may be arranged to deposit films on a multiplicity of substrates simultaneously, such as for example 2"×2" square substrates. The system may also be arranged for the simultaneous loading of a number of different targets, to facilitate effective deposition formation of multi-layer heterostructures.

The heterostructures may be produced at a desired thickness, as for example by using a thickness monitor, such as a QCM thickness monitor, for achieving precise control of thicknesses of each layer of the heterostructure. The substrate may optionally be heated, e.g., using a heating lamp or other heating means or techniques, to produce smoother films than are otherwise possible in the absence of heating.

Growth of alloys of various compositions in such manner requires alloy targets. These targets are readily commercially available, and may also be formed in the system by melting known amounts of the constituent metals by e-beam in the crucible.

Alternatively, the hydrogen sensor devices of the invention may be fabricated with formation of the component films of the device by chemical vapor deposition, as for example with the use of an ultra-high vacuum (UHV) CVD system.

Such a system may consist of a tube furnace connected to a diffusion pump via suitable fittings, e.g., 2" UltraTorr® fittings. A gas manifold, equipped with mass flow controllers, may be employed to provide carrier and reactive (e.g., $H_2$) gases in any desired combination. The base vacuum in such system may be monitored with appropriate means, such as a Pirani and a cold cathode gauge are attached, downstream of a liquid nitrogen cold trap.

The precursors may be delivered via solid bubblers or as solutions via a direct injection system. The liquid injection system allows for the rapid screening of a wide range of dopant levels. This system can achieve low vacuum levels, such as on the level of $5 \times 10^{-6}$ Torr. Such low pressure levels help to minimize the amount of residual oxygen in the CVD chamber.

A particular advantage of film growth by CVD is the smoothness of the films that are produced. For example, very smooth Pt films can be grown using $Cp'PtNe_3$ ($Cp'$=Methylcyclopentadienyl) as the precursor for the Pt deposition by CVD. The compound is extremely volatile, showing complete weight loss by 135° C. in atmospheric argon.

No heating element, explosion-proof housing or calibration are required for the hydrogen sensor device of the present invention, as have been necessary features in prior art systems. The lack of a need for such expensive heating, containment, and calibration apparatus significantly decreases the price, size and weight of the hydrogen sensor of the present invention.

The hydrogen sensor of the present invention can be readily constructed as a miniaturized optical fiber-based sensor. In addition to being extremely light-weight and requiring very little power, the construction of the hydrogen sensor of the present invention as a miniaturized optical fiber-based sensor allows for the employment of a large number of such sensors in arrays or rings in close proximity to areas of potential hydrogen leaks. The ability to remotely sense hydrogen concentrations in proximity to potential leak spots, by a multiplicity of small, easily deployed optical fiber-based sensor devices, enhances the safety, detection sensitivity and accuracy of the hydrogen sensing operation.

The hydrogen sensor of the invention may be conveniently fabricated as a solid-state device, of very small size and weight.

When the physical property change of the rare earth metal thin film is optical in character, transitioning from a divalent hydride of an opaque or otherwise optically non-transmissive (mirror or reflective) metal form to a trivalent hydride of an optically transmissive semiconducting form, it may be desirable to utilize a substrate that is optically transparent, such as a quartz, silica, or transparent ceramic material. Generally, any suitable substrate material of construction may be employed, including metals, ceramics, high temperature polymeric materials, etc.

Another embodiment of the present invention utilizes the hydrogen-sensitive films as cheap and simple visual tags for the detection of $H_2$. Such tags ca switch between a mirror-like state and a bright color such as red (readily achieved by coloring the glass substrate), and thus are amenable to visual inspection as well as to instrumental detection (e.g., by use of colorimetric detectors arranged in sensing relationship to the visual tag, such as may be desired in remote or hazardous environments).

For example, such tags can be supplied with $H_2$ tanks sold commercially, resulting in greater safety in the shipping, handling and storage of $H_2$.

The hydrogen detection apparatus and method of the present invention also have the advantage that unlike thermal conductivity sensors that require an air balance composition to detect hydrogen, the rare earth metal thin film sensing system can detect hydrogen in a totally inert atmosphere.

Further, since all of the instrument electronics associated with the hydrogen sensor of the present invention may by remotely located, e.g., several hundred feet from the rare earth metal thin film sensor element, using a light source introduced to the rare earth metal thin film via fiber optic cables, and with the reflected light signal collected via fiber optic cable, the hydrogen sensor of the invention may be safely employed in a potentially flammable and/or explosive environment.

In less hazardous environments, such as a semiconductor manufacturing facility, a light source, the rare earth metal thin film sensor, and a signal detector may be incorporated in a single, self-contained unit. Alternately, a single light source and a single detector may be arranged to cycle between several rare earth metal thin film sensors distributed over the area to be monitored.

It will be appreciated that the hydrogen sensor of the present invention may thus be provided in a wide variety of potentially useful configurations, for a corresponding variety of hydrogen sensing applications. For example, the hydrogen sensor may be provided in the form of a portable, hand-held, battery-operated device.

The features and advantages of the present invention are more fully shown by the following non-limiting examples.

EXAMPLE 1

Deposition of a Palladium Thin Film

Due to the sensitivity of rare earth amides to moisture and oxygen, and their substantially reduced volatility, an ultra high vacuum (UHV) CVD system was employed.

For the chemical vapor deposition of the palladium protective layer, $Pd(hfac)_2$ was synthesized as the source reagent precursor for Pd.

$Pd(hfac)_2$ was synthesized by reacting, one equivalent of $PdCl_2$ $(CH_3CN)_2$ with two equivalents of Na(hfac). The $PdCl_2$ $(CH_3CN)_2$ required for this step was synthesized by carrying out a soxhlet extraction of $PdCl_2$ with $CH_3CN$.

The $^1H$ NMR of $Pd(hfac)_2$ shows a single resonance at 5.88 ppm. The DSC of the compound reveals a sharp melting at 103.7° C. followed by an endotherm, indicating vaporization, at 166.2° C. The TGA trace reveals complete vaporization by 175° C., making this an attractive precursor for the deposition of the protective palladium metal overcoat.

CVD film growth experiments conducted with $Pd(hfac)_2$ in the presence of forming gas (95% $N_2$, 5% H2) resulted in the deposition of high quality Pd films. Films deposited on glass were smooth and transparent. The transparency of the film was due the thinness of the deposited Pd layer (<100 D). The films were smooth, displaying an average root mean square (RMS) roughness of only 2.45 nm. This evidences the ability to grow conformal Pd films at very low thicknesses for the protective over-layer, thereby making the sensor extremely sensitive to hydrogen.

EXAMPLE 2

Deposition of Lanthanum in a Multilayer Structure

The deposition of lanthanum in a multi-layer structure was carried out, to form a structure including a thin Pd layer deposited on a polished quartz substrate and overlaid by a thicker lanthanum layer, with a thin Pd protective layer capping the La layer.

The initial Pd layer was grown at ~5 torr with a substrate temperature of 250° C. The film growth was carried out under the reducing atmosphere of forming gas (95% $N_2$, 5% $H_2$). The subsequent La layer was grown at a substrate temperature of 350° C. in the same reducing atmosphere.

The conditions for the final protective Pd film were identical to those of the first deposited Pd layer.

The final product was a transparent, smooth film. The EDS spectrum of the film clearly indicated the presence of both lanthanum and palladium in the film.

EXAMPLE 3

Thin Film Deposition of Yttrium by Physical Vapor Deposition

Vacuum refined yttrium lumps (99.9%) and Pd pellets (99.9%) were melted in an electron beam PVD tool and used as targets. Depositions were carried out on polished, high grade, quartz photomask blanks. A deposition methodology was established by trial and error that ensured the exclusion of oxygen and moisture in the deposition chamber. A 150 Å thick layer of Pd was determined to be necessary to protect the sensory yttrium layer.

An AFM topographical image of one of the films showed that the root mean square (RMS) roughness of the Pd overlayer was 10.8 nm which was more than that of the film grown by CVD (2.5 nm). The $R_{max}$ of the film grown by PVD was also more than that of the film grown by CVD. Nevertheless, films grown by PVD are visibly smooth and reflective, in relation to the films grown by CVD.

EXAMPLE 4

Effects of Exposure of Rare Earth Metal Thin Films to Hydrogen

Strips of rare earth metal thin films were placed in a 1 inch diameter quartz CVD tube and exposed to slightly less than one atmosphere (700 Torr) of hydrogen. The color of the film turned yellowish within 2–3 minutes, indicating the permanent conversion of Y to $YH_2$.

Within a minute of this color change the film displayed a striking change in optical transmission, changing from opaque and reflective to transparent. This optical change is reversible and provides a reversible hydrogen sensor. Upon removal of hydrogen an immediate loss of transparency was noted although complete opacity was restored after only several hours. This demonstrates the suitability of rare earth metal thin films for inexpensive, hydrogen-specific, optical sensors in accordance with the present invention.

EXAMPLE 5

Hydrogen Selectivity of Rare Earth Metal Thin Films

A series of film growth experiments was carried out to determine the effect of film thickness both on stress and on the sensory properties of the film. Three sets of films (4 each) with yttrium thicknesses of 2500, 4000 and 5000 Å were grown. Each film had a 150 D Pd overlayer deposited thereon.

The selectivity of the sensor was demonstrated by optical change from opaque to clear when the films were exposed to:

1) hydrogen diluted in 50% nitrogen;
2) hydrogen-saturated pentane vapors, thereby presenting hydrogen to the sensor in a low boiling organic solvent; and
3) hydrogen diluted with 50% ammonia.

These results demonstrated the selectivity of the sensor of the present invention. We are unaware of any commercially available sensor can detect hydrogen under any of the above conditions (1)–(3).

While the invention has been described herein with reference to various illustrative features, aspects and embodiments, it will be recognized that the utility of the invention is not thus limited, but rather extends to and encompasses other variations, modifications and other embodiments of the invention. Accordingly, the invention is intended to be correspondingly interpreted and construed as embracing all such variations, modifications and other embodiments within the spirit and scope of the ensuing claims.

What is claimed is:

1. A hydrogen sensor for the detection of hydrogen gas in a gaseous environment susceptible to the incursion or generation of hydrogen, said sensor comprising
   (i) a rare earth metal thin film, consisting essentially of one or more metals selected from the group consisting of scandium, yttrium, lanthanum cerium, praseodymium, neodymium, promethium, samarium, europium, gadolinium, terbium, dysprosium, holmium, erbium, thulium, ytterbium, lutetium, actinium, thorium, protactinium, uranium, neptunium, plutonium, americium, curium, berkelium, californium, einsteinium, fermium, mendelevium, nobelium, lawrencium, and alloys thereof with one or more of magnesium, calcium, barium, strontium, cobalt and iridium, said rare earth metal thin film exhibiting a detectable change of physical property when the rare earth metal thin film is exposed to hydrogen gas in a gaseous environment, wherein the rare earth metal thin film is arranged for exposure to the gaseous environment susceptible to the incursion or generation of hydrogen and
   (ii) means for exhibiting the detectable change of physical property when the rare earth metal thin film is exposed to hydrogen in said gaseous environment, said means including circuitry for signal processing the change of physical property and generating an output indicative of hydrogen gas, and wherein the sensor does not comprise a source of hydrogen arranged for selectively switching the rare earth metal thin film between respective switched states.

2. A hydrogen sensor according to claim 1, wherein the physical property is selected from the group consisting of optical transmissivity, electrical resistivity, magnetoresistance and photoconductivity.

3. A hydrogen sensor according to claim 1, further comprising an output assembly for converting the physical property change to a perceivable output selected from the group consisting of visual outputs, auditory outputs, tactile outputs, and auditory outputs.

4. A hydrogen sensor according to claim 1, wherein the rare earth metal thin film consists essentially of a trivalent rare earth metal reactive with hydrogen to form both metal dihydride and metal trihydride reaction products, wherein the metal dihydride and metal trihydride reaction products have differing physical properties.

5. A hydrogen sensor according to claim 1, wherein the physical property change comprises a change of optical opacity to optical transparency when the rare earth metal thin film is contacted with hydrogen gas.

6. A hydrogen sensor according to claim 1, further including a monitor operatively arranged in monitoring relationship to the rare earth metal thin film to provide an output indicative of the presence of hydrogen.

7. A hydrogen sensor according to claim 1, wherein the physical property change comprises a change from a metallic state to a semiconducting state.

8. A hydrogen sensor according to claim 1, further including an electrical resistance monitor operatively arranged in monitoring relationship to the rare earth metal thin film to provide an output indicative of the presence of hydrogen in the environment.

9. A hydrogen sensor according to claim 1, wherein the rare earth metal thin film consists essentially of yttrium, and the physical property change comprises a change of optical transmissivity when the rare earth metal thin film is contacted with hydrogen gas, from a reflecting yttrium dihydride metallic state to a transparent yttrium trihydride semiconducting state, and a substantially isothermal change of optical transmissivity when hydrogen gas is removed from the rare earth metal thin film, from a transparent yttrium trihydride semiconducting state to a reflecting yttrium dihydride metallic state.

10. A hydrogen sensor according to claim 1, wherein the rare earth metal thin film is overlaid by a hydrogen-permeable material comprising a metal selected from the group consisting of Pd, Pt, Ir, Mg, Ca, Ag, Au, Co, and alloys thereof.

11. A hydrogen sensor according to claim 1, wherein the rare earth metal thin film is overlaid by a hydrogen-permeable material that is doped with a dopant selected from the group consisting of Mg, Ca, Al, Ir and Co.

12. A hydrogen sensor according to claim 1, wherein the rare earth metal thin film is overlaid by a thin film of a material including a metal selected from the group consisting of palladium, platinum, and iridium.

13. A hydrogen sensor according to claim 1, having on the rare earth metal film a hydrogen-permeable protective overlayer comprising alternating doped and undoped material layers.

14. A hydrogen sensor according to claim 13, wherein the doped material layers comprise a material selected from the group consisting of Pd, Ir and Pt, doped with a dopant species selected from the group consisting of Mg and Al, and wherein the undoped material layers comprise a material selected from the group consisting of Pd, Ir and Pt.

15. A hydrogen gas detection system for monitoring a gaseous environment in an extended or remote area region that is susceptible to the incursion or generation of hydrogen gas therein, said hydrogen gas detection system comprising a multiplicity of hydrogen sensors as in claim 1, each of which is arranged for detection of hydrogen gas in a specific different individual locus of the extended area region.

16. A hydrogen detection system according to claim 15, wherein the physical property that is detectably changed comprises a physical property selected from the group consisting of optical transmissivity, electrical resistivity, magneto-resistance and photoconductivity.

17. A hydrogen detection system according to claim 15, constructed and arranged so that different physical properties are detected when multiple hydrogen sensors are contacted with hydrogen at different loci of the extended area region.

18. A hydrogen sensor according to claim 1, wherein said rare earth metal thin film has a thickness of from about 50 to about 2000 nm.

19. A hydrogen sensor according to claim 18, wherein said rare earth metal thin film has a protective overlayer thereon.

20. A hydrogen sensor according to claim 19, wherein the protective overlayer has a thickness of from about 2 to about 1000 nm.

21. A method of detecting hydrogen gas in a gaseous environment susceptible to the incursion or generation of hydrogen, comprising:

providing a hydrogen sensor as in claim 1;

exposing the rare earth metal thin film to the gaseous environment;

monitoring said physical property to determine the presence of hydrogen gas in the gaseous environment; and generating an output indicative of hydrogen gas in said gaseous environment.

22. A method according to claim 21, wherein said physical property comprises a property selected from the group consisting of optical transmissivity, electrical resistivity, magneto-resistance and photoconductivity.

23. A method according to claim 21, further comprising converting the physical property change to a perceivable output as part of said monitoring step, wherein the perceivable output includes an output selected from the group consisting of visual outputs, optical outputs, tactile outputs, and auditory outputs.

24. A method according to claim 21, wherein the physical property change comprises a change of optical opacity to optical transparency when the rare earth metal thin film is exposed to hydrogen.

25. A method according to claim 21, wherein the physical property change comprises a change from a metallic state to a semiconducting state.

26. A method according to claim 21, wherein the rare earth metal thin film consists essentially of a rare earth metal component selected from the group consisting of trivalent rare earth metals reactive with hydrogen to form both metal dihydride and metal trihydride reaction products, and wherein the metal dihydride and metal trihydride reaction products have differing physical properties.

27. A method according to claim 21, wherein the rare earth metal thin film is overlaid by a hydrogen-permeable material comprising a metal selected from the group consisting of Pd, Pt, Ir, Mg, Ca, Ag, Au, Co, and alloys thereof.

28. A method according to claim 21, wherein the rare earth metal thin film is overlaid by a hydrogen-permeable material that is doped with a dopant selected from the group consisting of Mg, Ca, Al, Ir and Co.

29. A method according to claim 21, wherein the rare earth metal thin film is overlaid by a thin film of a material including a metal selected from the group consisting of palladium, platinum, and iridium.

30. A method according to claim 21, wherein the rare earth metal film is overlaid with a hydrogen-permeable protective overlayer comprising alternating doped and undoped material layers.

31. A method according to claim 21, wherein the doped material layers comprise a material selected from the group consisting of Pd, Ir and Pt, doped with a dopant species selected from the group consisting of Mg and Al, and wherein the undoped material layers comprise a material selected from the group consisting of Pd, Ir and Pt.

32. A method according to claim 21, wherein the step of monitoring said physical property to determine the presence of hydrogen in the environment, comprises monitoring the electrical resistance of the rare earth metal thin film.

33. A method according to claim 21, wherein the rare earth metal thin film consists essentially of yttrium, and the physical property change comprises a change of optical transsmissivity when the rare earth metal thin film is contacted with hydrogen gas, from a reflecting yttrium dihydride metallic state to a transparent yttrium trihydride semiconducting state.

34. A hydrogen sensor for the continuous monitoring and detection of hydrogen gas in a gaseous environment susceptible to the incursion or generation of hydrogen, said sensor comprising a rare earth metal thin film, consisting essentially of one or more metals selected from the group consisting of scandium, yttrium, lanthanum, cerium, praseodymium, neodymium, promethium, samarium, europium, gadolinium, terbium, dysprosium, holmium, erbium, thulium, ytterbium, lutetium, actinium, thorium, protactinium, uranium, neptunium, plutonium, americium, curium, berkelium, californium, einsteinium, fermium, mendelevium, nobelium, lawrencium, and alloys thereof with one or more of magnesium, calcium, barium, strontium, cobalt and iridium, said rare earth metal thin film exhibiting a detectable change of physical property when the rare earth metal thin film is exposed to hydrogen gas in a gaseous environment, wherein the rare earth metal thin film is arranged for exposure to the gaseous environment susceptible to the incursion or generation of hydrogen; and means for exhibiting the detectable change of physical property when the rare earth metal thin film is exposed to hydrogen in said gaseous environment, said means including circuitry for signal processing the change of physical property and generating an output indicative of the concentration of hydrogen gas, and wherein the sensor does not comprise a source of hydrogen arranged for selectively switching the rare earth metal thin film between respective switched states;

wherein the rare earth metal thin film is hydridified in exposure to hydrogen gas when present in said gaseous environment, and said rare earth metal thin film changes said physical property in proportion to hydrogen concentration in said gaseous environment, by forming rare earth metal hydride in response to the hydrogen concentration in said gaseous environment.

35. The hydrogen sensor of claim 34, further comprising an optical fiber operatively coupled at a first end thereof with a signal generating and processing assembly, and having said rare earth metal thin film as a coating on a second end of the optical fiber, with said signal generating and processing assembly including (i) a light source arranged for generating a light signal and transmitting same along the optical fiber toward the second end thereof for impingement of the light signal on the rare earth metal thin film coating and (ii) a light detector arranged for receiving reflected light signal transmitted along the optical fiber from the rare earth metal thin film coating during impingement of the generated light signal on the rare earth metal thin film coating, whereby light detected by the light detector provides an optical transmissivity signal to the circuitry for generating said output indicative of the concentration of hydrogen gas in said gaseous environment.

36. The hydrogen sensor of claim 35, wherein the optical fiber is cladded along its length, and is branched at the first end thereof, with a first branch being coupled with the light source and a second branch being coupled with the light detector.

37. The hydrogen sensor of claim 35, wherein the light source comprises a light emitting diode.

38. The hydrogen sensor of claim 35, wherein the rare earth metal thin film coating comprises yttrium.

39. The hydrogen sensor of claim 34, wherein the rare earth metal thin film is overlaid by a thin film hydrogen-permeable protective overlayer.

40. The hydrogen sensor of claim 39, wherein the hydrogen-permeable protective overlayer comprises palladium.

41. The hydrogen sensor of claim 39, wherein the hydrogen-permeable protective overlayer comprises alternating doped and undoped layers.

42. A method of continuously monitoring the concentration of hydrogen gas in a gaseous environment susceptible to the incursion or generation of hydrogen, by the steps including:

providing a hydrogen sensor comprising a rare earth metal thin film, consisting essentially of one or more metals selected from the group consisting of scandium, yttrium, lanthanum, cerium, praseodymium, neodymium, promethium, samarium, europium, gadolinium, terbium, dysprosium, holmium, erbium, thulium, ytterbium, lutetium, actinium, thorium, protactinium, uranium, neptunium, plutonium, americium, curium, berkelium, californium, einsteinium, fermium, mendelevium, nobelium, lawrencium, and alloys thereof with one or more of magnesium, calcium, barium, strontium, cobalt and iridium, said rare earth metal thin film exhibiting a detectable change of physical property when the rare earth metal thin film is exposed to hydrogen gas in a gaseous environment, wherein the rare earth metal thin film is arranged for exposure to the gaseous environment susceptible to the incursion or generation of hydrogen; and means for exhibiting the detectable change of physical property when the rare earth metal thin film is exposed to hydrogen in said gaseous environment, said means including circuitry for signal processing the change of physical property and generating an output indicative of the concentration of hydrogen gas, and wherein the sensor does not comprise a source of hydrogen arranged for selectively switching the rare earth metal thin film between respective switched states;

exposing the rare earth metal thin film to the gaseous environment, whereby the rare earth metal thin film is hydridified in exposure to hydrogen gas when present in said gaseous environment, and said rare earth metal thin film changes said physical property in proportion to hydrogen concentration in said gaseous environment, by forming rare earth metal hydride in response to the hydrogen concentration in said gaseous environment;

monitoring said physical property to determine the concentration of hydrogen gas in the gaseous environment; and generating an output indicative of the concentration of hydrogen gas in said gaseous environment.

43. The method of claim 42, wherein the hydrogen sensor comprises an optical fiber operatively coupled at a first end thereof with a signal generating and processing assembly, and having said rare earth metal thin film as a coating on a second end of the optical fiber, with said signal generating and processing assembly including (i) a light source arranged for generating a light signal and transmitting same along the optical fiber toward the second end thereof for impingement of the light signal on the rare earth metal thin film coating and (ii) a light detector arranged for receiving reflected light signal transmitted along the optical fiber from the rare earth metal thin film coating during impingement of the generated light signal on the rare earth metal thin film coating, whereby light detected by the light detector provides an optical transmissivity signal to the circuitry for generating said output indicative of the concentration of hydrogen gas in said gaseous environment.

44. The method of claim 43, wherein the optical fiber is cladded along its length, and is branched at the first end thereof, with a first branch being coupled with the light source and a second branch being coupled with the light detector.

45. The method of claim 43, wherein the light source comprises a light emitting diode.

46. The method of claim 42, wherein the rare earth metal thin film coating comprises yttrium.

47. The method of claim 42, wherein the rare earth metal thin film is overlaid by a thin film hydrogen-permeable protective overlayer.

48. The method of claim 47, wherein the hydrogen-permeable protective overlayer comprises palladium.

49. The method of claim 47, wherein the hydrogen-permeable protective overlayer comprises alternating doped and undoped layers.

* * * * *

UNITED STATES PATENT AND TRADEMARK OFFICE
CERTIFICATE OF CORRECTION

PATENT NO. : 6,006,582
DATED : December 28, 1999
INVENTOR(S) : Gautam Bhandari and Thomas H. Baum It is certified that error appears in the above-identified patent and that said Letters Patent is hereby corrected as shown below:

Drawings 4, 8, and 9,
The "clear blocks" should be labeled as laid out in Amendment Responding to March 4, 1999 Office Action.

Column 9,
Line 37, after "substrate." start a new paragraph.

Column 11,
Line 28, change "O=⟨R'" to --O=⟨R"--.
Line 34, change "R"N=⟨R'" to --R"N=⟨R"--.

Column 19,
Line 40, change "foi msing" to -- forming --.

Column 21,
Line 32, change "Cp'PtNe₃" to -- Cp'PtMe₃ --.

Column 22,
Line 3, change "ca" to -- can --.

Signed and Sealed this

Twenty-fifth Day of December, 2001

Attest:

*Attesting Officer*

JAMES E. ROGAN
*Director of the United States Patent and Trademark Office*